(12) United States Patent
Fiebig et al.

(10) Patent No.: US 9,955,955 B2
(45) Date of Patent: May 1, 2018

(54) BIOPSY DEVICE WITH SLIDE-IN PROBE

(71) Applicant: Devicor Medical Products, Inc., Cincinnati, OH (US)

(72) Inventors: Kevin M. Fiebig, Cincinnati, OH (US); John A. Hibner, Mason, OH (US); Edward A. Rhad, Fairfield, OH (US); John S. Ehlert, Cincinnati, OH (US); Morgan R. Hunter, Cincinnati, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 567 days.

(21) Appl. No.: 13/762,774

(22) Filed: Feb. 8, 2013

(65) Prior Publication Data

US 2013/0150751 A1 Jun. 13, 2013

Related U.S. Application Data

(63) Continuation-in-part of application No. 13/693,671, filed on Dec. 4, 2012.
(Continued)

(51) Int. Cl.
*A61B 10/02* (2006.01)
*A61B 8/08* (2006.01)
*A61B 17/00* (2006.01)

(52) U.S. Cl.
CPC ........ *A61B 10/0275* (2013.01); *A61B 8/0841* (2013.01); *A61B 10/0283* (2013.01);
(Continued)

(58) Field of Classification Search
None
See application file for complete search history.

(56) References Cited

U.S. PATENT DOCUMENTS 4,473,070 A    9/1984   Matthews et al.
5,470,305 A *  11/1995  Arnett et al. ............... 601/161
(Continued)

FOREIGN PATENT DOCUMENTS

CN    101011268 A    8/2007
CN    101095619 A    1/2008
(Continued)

OTHER PUBLICATIONS

International Search Report and Written Opinion dated Mar. 13, 2013 for Application No. PCT/US2012/067823.
(Continued)

*Primary Examiner* — Matthew Kremer
(74) *Attorney, Agent, or Firm* — Frost Brown Todd LLC

(57) ABSTRACT

An exemplary ultrasound biopsy device includes a probe and a holster. The probe is insertable into the holster to form a completed assembly. To assemble the probe to the holster, the probe is initially slid laterally onto the holster and then slid forward to latch the probe into engagement with the holster. The holster is coupled to a vacuum control module by one or more conduits and a power cable. The conduits and/or power cable may be retracted into the vacuum control module. The probe of the biopsy device includes a blade assembly at the distal end. The blade assembly comprises a blade that snaps onto a nosecone via a pair of resilient notched ends. A frictional fitting needle cover can be inserted over the needle and blade assembly to protect the user from the sharp blade.

20 Claims, 17 Drawing Sheets

Related U.S. Application Data

(60) Provisional application No. 61/566,793, filed on Dec. 5, 2011.

(52) U.S. Cl.
CPC ............. *A61B 2010/0208* (2013.01); *A61B 2010/0225* (2013.01); *A61B 2017/0046* (2013.01)

(56) References Cited

U.S. PATENT DOCUMENTS

| | | | |
|---|---|---|---|
| 5,526,822 A | 6/1996 | Burbank et al. | |
| 5,609,604 A | 3/1997 | Schwemberger et al. | |
| 5,928,164 A | 7/1999 | Burbank et al. | |
| 6,017,316 A | 1/2000 | Ritchart et al. | |
| 6,086,544 A | 7/2000 | Hibner et al. | |
| 6,162,187 A | 12/2000 | Buzzard et al. | |
| 6,273,862 B1 | 8/2001 | Privitera et al. | |
| 6,428,487 B1 | 8/2002 | Burdorff et al. | |
| 6,432,065 B1 | 8/2002 | Burdorff et al. | |
| 6,497,226 B2 | 12/2002 | Bircann et al. | |
| 6,602,203 B2 | 8/2003 | Stephens et al. | |
| 6,626,849 B2 | 9/2003 | Huitema et al. | |
| 6,752,768 B2 | 6/2004 | Burdorff et al. | |
| 7,140,109 B2 | 11/2006 | Dourlens et al. | |
| 7,442,171 B2 | 10/2008 | Stephens et al. | |
| 7,491,177 B2 | 2/2009 | Hibner | |
| 7,648,466 B2 | 1/2010 | Stephens et al. | |
| 7,837,632 B2 | 11/2010 | Stephens et al. | |
| 7,854,706 B2 | 12/2010 | Hibner | |
| 7,858,038 B2 | 12/2010 | Andreyko et al. | |
| 7,914,464 B2 | 3/2011 | Burdorff et al. | |
| 7,938,786 B2 | 5/2011 | Ritchie et al. | |
| 8,075,495 B2 | 12/2011 | Andreyko et al. | |
| 8,083,687 B2 | 12/2011 | Parihar | |
| 8,109,885 B2 | 2/2012 | Heske et al. | |
| 8,118,755 B2 | 2/2012 | Hibner et al. | |
| 8,187,204 B2 | 5/2012 | Miller et al. | |
| 8,206,316 B2 | 6/2012 | Hibner et al. | |
| 8,206,409 B2 | 6/2012 | Privitera et al. | |
| 8,241,226 B2 | 8/2012 | Hibner et al. | |
| 8,241,301 B2 | 8/2012 | Zhang et al. | |
| 8,277,394 B2 | 10/2012 | Hibner | |
| 8,313,444 B2 | 11/2012 | Thompson et al. | |
| 8,366,635 B2 | 2/2013 | Parihar et al. | |
| 8,376,957 B2 | 2/2013 | Hibner et al. | |
| 8,379,957 B2 | 2/2013 | Slabaugh et al. | |
| 8,454,531 B2 | 6/2013 | Speeg et al. | |
| 8,702,623 B2 | 4/2014 | Parihar et al. | |
| 8,764,680 B2 | 7/2014 | Rhad et al. | |
| 8,801,742 B2 | 8/2014 | Rhad et al. | |
| 8,858,465 B2 | 10/2014 | Fiebig | |
| 8,938,285 B2 | 1/2015 | Fiebig et al. | |
| 9,095,326 B2 | 8/2015 | Ritchie et al. | |
| 9,486,186 B2 | 11/2016 | Fiebig et al. | |
| 2001/0047183 A1 | 11/2001 | Privitera et al. | |
| 2004/0249307 A1* | 12/2004 | Thompson et al. | 600/568 |
| 2006/0074345 A1 | 4/2006 | Hibner | |
| 2008/0146965 A1 | 6/2008 | Privitera et al. | |
| 2008/0200835 A1 | 8/2008 | Monson et al. | |
| 2008/0214955 A1 | 9/2008 | Speeg et al. | |
| 2008/0280540 A1 | 11/2008 | Johnson | |
| 2009/0087249 A1 | 4/2009 | Flagle et al. | |
| 2009/0131821 A1 | 5/2009 | Speeg et al. | |
| 2009/0318832 A1* | 12/2009 | Andreyko | A61B 10/0275 600/567 |
| 2010/0152610 A1 | 6/2010 | Parihar et al. | |
| 2010/0152615 A1 | 6/2010 | Mark et al. | |
| 2010/0160816 A1* | 6/2010 | Parihar | A61B 10/0275 600/564 |
| 2010/0160819 A1* | 6/2010 | Parihar et al. | 600/566 |
| 2012/0029354 A1 | 2/2012 | Mark et al. | |
| 2012/0157879 A1 | 6/2012 | Mark et al. | |
| 2013/0053724 A1 | 2/2013 | Fiebig et al. | |
| 2013/0079665 A1 | 3/2013 | Hibner et al. | |
| 2013/0324882 A1 | 12/2013 | Mescher | |

FOREIGN PATENT DOCUMENTS

| | | |
|---|---|---|
| EP | 0 268 641 | 9/1993 |
| EP | 1126186 A2 | 8/2001 |
| EP | 1872726 A1 | 1/2008 |
| JP | 2000-316867 A | 11/2000 |
| JP | 2007-330785 A | 12/2007 |
| JP | 2009-125587 A | 6/2009 |
| WO | WO 87/06815 | 11/1987 |

OTHER PUBLICATIONS

Chinese First Office Action dated Jul. 24, 2015 for Appl. No. 2012800596555, 14 pgs.
Supplementary Partial European Search Report dated Jun. 11, 2015 for Appl. No. 12855086.0, 6 pgs.
Australian Office Action dated Feb. 7, 2017 for Application No. AU 2012348030, 4 pgs.
Australian Office Action dated Oct. 12, 2017 for Application No. AU 2013248030, 4 pgs.
Chinese Office Action dated Mar. 10, 2016 for Application No. CN 201280059655.5, 5 pgs.
Chinese Office Action dated Aug. 5, 2016 for Application No. CN 201280059655.5, 5 pgs.
European Communication dated Oct. 7, 2016 for Application No. EP 12855086.0, 7 pgs.
Supplementary European Search Report and Written Opinion dated Oct. 19, 2015 for Application No. EP12855086.0, 10 pgs.
U.S. Appl. No. 61/566,793, filed Dec. 5, 2011.
U.S. Appl. No. 61/598,939, filed Feb. 15, 2012.
U.S. Appl. No. 61/727,889, filed Nov. 19, 2012.

* cited by examiner

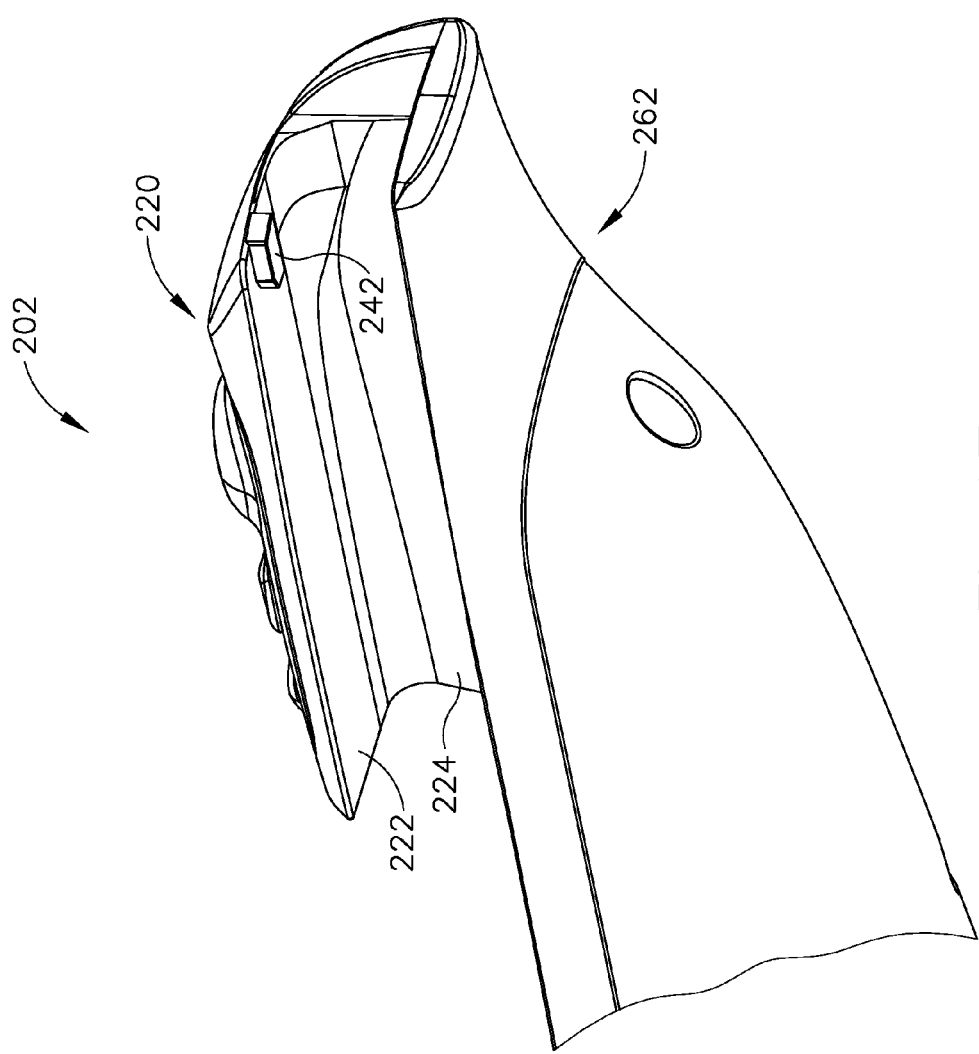

BIOPSY DEVICE WITH SLIDE-IN PROBE

PRIORITY

This application is a continuation-in-part of U.S. patent application Ser. No. 13/693,671, entitled "Biopsy Device with Slide-In Probe," filed Dec. 4, 2012, which claims priority to U.S. Provisional Patent Application No. 61/566,793, entitled "Biopsy Device with Slide-In Probe," filed Dec. 5, 2011, the disclosures of which are incorporated by reference herein.

BACKGROUND

Biopsy samples have been obtained in a variety of ways in various medical procedures using a variety of devices. Biopsy devices may be used under stereotactic guidance, ultrasound guidance, MRI guidance, PEM guidance, BSGI guidance, or otherwise. For instance, some biopsy devices may be fully operable by a user using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other biopsy devices may be fully or at least partially operable without being tethered or otherwise connected with another device.

Merely exemplary biopsy devices and biopsy system components are disclosed in U.S. Pat. No. 5,526,822, entitled "Method and Apparatus for Automated Biopsy and Collection of Soft Tissue," issued Jun. 18, 1996; U.S. Pat. No. 5,928,164, entitled "Apparatus for Automated Biopsy and Collection of Soft Tissue," issued Jul. 27, 1999; U.S. Pat. No. 6,017,316, entitled "Vacuum Control System and Method for Automated Biopsy Device," issued Jan. 25, 2000; U.S. Pat. No. 6,086,544, entitled "Control Apparatus for an Automated Surgical Biopsy Device," issued Jul. 11, 2000; U.S. Pat. No. 6,162,187, entitled "Fluid Collection Apparatus for a Surgical Device," issued Dec. 19, 2000; U.S. Pat. No. 6,432,065, entitled "Method for Using a Surgical Biopsy System with Remote Control for Selecting an Operational Mode," issued Aug. 13, 2002; U.S. Pat. No. 6,626,849, entitled "MRI Compatible Surgical Biopsy Device," issued Sep. 11, 2003; U.S. Pat. No. 6,752,768, entitled "Surgical Biopsy System with Remote Control for Selecting an Operational Mode," issued Jun. 22, 2004; U.S. Pat. No. 7,442,171, entitled "Remote Thumbwheel for a Surgical Biopsy Device," issued Oct. 8, 2008; U.S. Pat. No. 7,648,466, entitled "Manually Rotatable Piercer," issued Jan. 19, 2010; U.S. Pat. No. 7,837,632, entitled "Biopsy Device Tissue Port Adjustment," issued Nov. 23, 2010; U.S. Pat. No. 7,854,706, entitled "Clutch and Valving System for Tetherless Biopsy Device," issued Dec. 1, 2010; U.S. Pat. No. 7,914,464, entitled "Surgical Biopsy System with Remote Control for Selecting an Operational Mode," issued Mar. 29, 2011; U.S. Pat. No. 7,938,786, entitled "Vacuum Timing Algorithm for Biopsy Device," issued May 10, 2011; U.S. Pat. No. 8,083,687, entitled "Tissue Biopsy Device with Rotatably Linked Thumbwheel and Tissue Sample Holder," issued Dec. 21, 2011; and U.S. Pat. No. 8,118,755, entitled "Biopsy Sample Storage," issued Feb. 21, 2012. The disclosure of each of the above-cited U.S. Patents is incorporated by reference herein.

Additional exemplary biopsy devices and biopsy system components are disclosed in U.S. Pat. Pub. No. 2006/0074345, entitled "Biopsy Apparatus and Method," published Apr. 6, 2006; U.S. Pat. Pub. No. 2008/0146962, entitled "Biopsy System with Vacuum Control Module," published Jun. 19, 2008; U.S. Pat. Pub. No. 2008/0214955, entitled "Presentation of Biopsy Sample by Biopsy Device," published Sep. 4, 2008; U.S. Pat. Pub. No. 2008/0221480, entitled "Biopsy Sample Storage," published Sep. 11, 2008; U.S. Pat. Pub. No. 2009/0131821, entitled "Graphical User Interface For Biopsy System Control Module," published May 21, 2009; U.S. Pat. Pub. No. 2009/0131820, entitled "Icon-Based User Interface on Biopsy System Control Module," published May 21, 2009; U.S. Pat. Pub. No. 2010/0113973, entitled "Biopsy Device with Rotatable Tissue Sample Holder," published May 6, 2010; U.S. Pat. Pub. No. 2010/0152610, entitled "Hand Actuated Tetherless Biopsy Device with Pistol Grip," published Jun. 17, 2010; U.S. Pat. Pub. No. 2010/0160819, entitled "Biopsy Device with Central Thumbwheel," published Jun. 24, 2010; U.S. Pat. Pub. No. 2010/0160824, entitled "Biopsy Device with Discrete Tissue Chambers," published Jun. 24, 2010; U.S. Pat. Pub. No. 2010/0317997, entitled "Tetherless Biopsy Device with Reusable Portion," published Dec. 16, 2010; U.S. Pat. Pub. No. 2012/0109007, entitled "Handheld Biopsy Device with Needle Firing," published May 3, 2012; U.S. Non-Provisional patent application Ser. No. 13/086,567, entitled "Biopsy Device with Motorized Needle Firing," filed Apr. 14, 2011; U.S. Non-Provisional patent application Ser. No. 13/150,950, entitled "Needle Assembly and Blade Assembly for Biopsy Device," filed Jun. 1, 2011; U.S. Non-Provisional patent application Ser. No. 13/205,189, entitled "Access Chamber and Markers for Biopsy Device," filed Aug. 8, 2011; U.S. Non-Provisional patent application Ser. No. 13/218,656, entitled "Biopsy Device Tissue Sample Holder with Bulk Chamber and Pathology Chamber," filed Aug. 26, 2011; U.S. Provisional Patent App. No. 61/566,793, entitled "Biopsy Device With Slide-In Probe," filed Dec. 5, 2011; U.S. Non-Provisional patent application Ser. No. 13/483,235, entitled "Control for Biopsy Device," filed May 30, 2012; and U.S. Provisional Patent App. No. 61/727,889, entitled "Biopsy System with Graphical User Interface," filed Nov. 19, 2012. The disclosure of each of the above-cited U.S. Patent Application Publications, U.S. Non-Provisional Patent Applications, and U.S. Provisional Patent Applications is incorporated by reference herein.

While several systems and methods have been made and used for obtaining a biopsy sample, it is believed that no one prior to the inventor has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 17 depicts a front perspective view of the holster of FIG. 3, showing a probe engagement feature.

Figure 1:
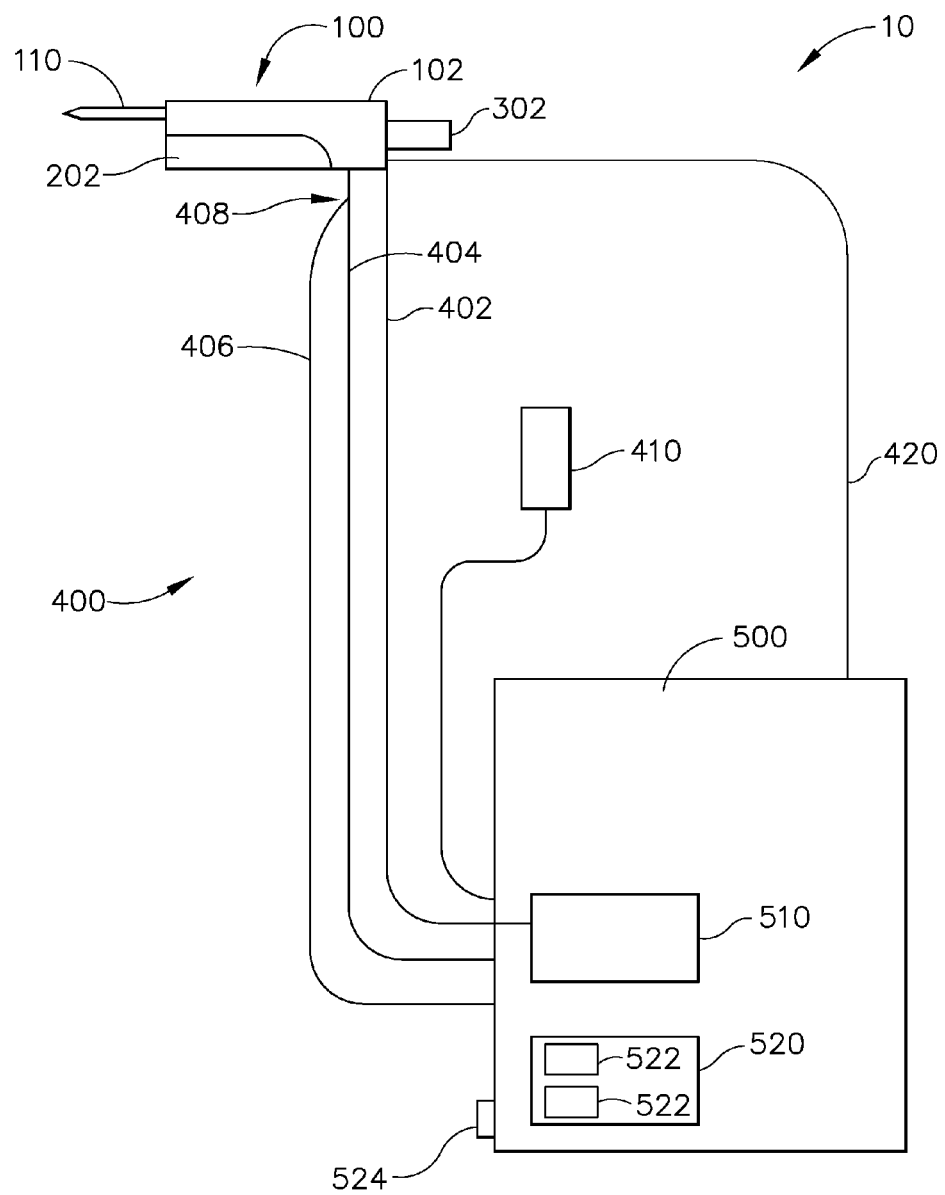
FIG. 1 depicts a schematic view of an exemplary biopsy system.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Biopsy System

FIG. 1 depicts an exemplary biopsy system (10) comprising a biopsy device (100), a plurality of conduits (400) and a vacuum control module (500). Biopsy device (100) comprises a holster (202) and a probe (102). A needle (110) extends distally from probe (102) and is inserted into a patient's tissue to obtain tissue samples as will be described in greater detail below. These tissue samples are deposited into a tissue sample holder (302) that is coupled to a proximal end of probe (102), as will also be describe in further detail below. Of course needle (110) and tissue sample holder (302) may be coupled to probe (102) at a range of locations. For instance, needle (110) may extend from the top of probe (102), from a side of probe (102), from the bottom of probe (102), or, may be omitted from probe (102) entirely. Tissue sample holder (302) may be coupled to the top of probe (102), to a side of probe (102), to the bottom of probe (102), or, may be omitted from probe (102) entirely. Probe (102) of the present example is separable from holster (202), though this is merely optional. It should also be understood that the use of the term "holster" herein should not be read as necessarily requiring any portion of probe (102) to be inserted into any portion of holster (202). While an notched upper control unit (220) of the holster (202) and a latch (190) of probe (102) are used to cooperatively removably secure probe (102) to holster (202), as shown in FIGS. 2-4 and 7 and described in greater detail below, it should be understood that a variety of other types of structures, components, features, etc. (e.g., bayonet mounts, prongs, clamps, clips, snap fittings, etc.) may be used to provide removable coupling of probe (102) and holster (202). Furthermore, in some biopsy devices (100), probe (102) and holster (202) may be of unitary or integral construction, such that the two components cannot be separated. By way of example only, in versions where probe (102) and holster (202) are provided as separable components, probe (102) may be provided as a disposable component, while holster (202) may be provided as a reusable component. Still other suitable structural and functional relationships between probe (102) and holster (202) will be apparent to those of ordinary skill in the art in view of the teachings herein.

Biopsy system (10) shown in FIG. 1 further includes a vacuum control module (500) that is fluidly coupled to biopsy device (100) via one or more conduits (400). In the present example, vacuum control module (500) comprises a vacuum source (510) operable to provide a vacuum to biopsy device (100). By way of example only, vacuum source (510) is contained within vacuum control module (500) and is fluidly coupled to probe (102) via a first conduit (402), such as flexible tubing. Of course, in addition or in the alternative, vacuum source (510) may be incorporated into probe (102), incorporated into holster (202), and/or be a separate component altogether. One merely exemplary biopsy device (100) having a vacuum source (510) incorporated therein is disclosed in U.S. Non-provisional patent application Ser. No. 12/953,715, entitled "Handheld Biopsy Device with Needle Firing," filed Nov. 24, 2010, the disclosure of which is incorporated by reference herein. As shown in FIG. 1, vacuum source (510) is in fluid communication with probe (102) and, as will be described in greater detail below, with needle (110). Thus, vacuum source (510) may be activated to draw tissue into a lateral aperture (112) of needle (110), described in more detail below. Vacuum source (510) is also in fluid communication with tissue sample holder (302) and a cutter (120). Vacuum source (510) of vacuum control module (500) may thus also be activated to draw severed tissue samples through a cutter lumen (122) of cutter (120) and into tissue sample holder (302). Of course other suitable configurations and uses for vacuum source (510) will be apparent to those of ordinary skill in the art in view of the teachings herein. It should also be understood that vacuum source (510) may simply be omitted, if desired.

In some versions, vacuum source (510) is provided in accordance with the teachings of U.S. Pat. Pub. No. 2008/0214955, entitled "Presentation of Biopsy Sample by Biopsy Device," published Sep. 4, 2008, the disclosure of which is incorporated by reference herein. As yet another merely illustrative example, vacuum source (510) may be provided in accordance with the teachings of U.S. Pat. Pub. No. 2011/0208086, entitled "Biopsy Device with Auxiliary Vacuum Source," published Aug. 25, 2011, the disclosure of which is incorporated by reference herein. Still other suitable ways in which vacuum source (510) may be provided will be apparent to those of ordinary skill in the art in view of the teachings herein.

A. Exemplary Vacuum Control Module and Conduits

Vacuum control module (500) of the present example is further fluidly coupled to biopsy device (100) by a second conduit (404) and a third conduit (406), such as flexible tubing, though one or both may be omitted. Third conduit (406) is in fluid communication with a saline bag (410) via vacuum control module (500). Saline bag (410) comprises saline fluid, though it should be understood that other fluids, gels, solids suspended in fluid, and/or other fluid-like materials may be used as will be apparent to one of ordinary skill in the art in view of the teachings herein. Of course it should be understood that saline bag (410) may be directly coupled to third conduit (406) and/or to biopsy device (100). Furthermore, in some versions, third conduit (406) is not coupled to vacuum control module (500), but may instead include a luer lock end (not shown) to which syringes (not shown) or other items may be coupled to deliver fluids, medicaments, and/or other items. Second conduit (404) is also fluidly coupled to vacuum control module (500) and provides filtered atmospheric air to the biopsy device (100) via a filter (not shown) in vacuum control module (500). As with third conduit (406), in some versions second conduit (404) is not coupled to vacuum control module (500), but and instead includes a luer lock end (not shown) or a filter (not shown). In the present example, second conduit (404) and third conduit (406) are joined together by a connector (408) prior to coupling to probe (102). Connector (408) may comprise a valve to seal either second or third conduit (404, 406) while the other conduit (404, 406) is in fluid communication with probe (102). Of course in other versions, connector (408) may comprise a Y-shaped connector to permit both second conduit (404) and third conduit (406) to be coupled to probe (102).

In some versions, conduits (400) may be coupled to a retraction system (520) of vacuum control module (500) such that first, second, and/or third conduit (402, 402, 406) may be retracted into vacuum control module (500) when not in use. By way of example only, retraction system (520) may comprise one or more spring-loaded spools (522) each sized to coil first, second, and/or third conduit (402, 404, 406) about spools (522). Spools (522) may be coupled to a ratchet assembly (not shown) such that when a user pulls on conduits (402, 404, 406), the ratchet assembly prevents spring-loaded spools from retracting conduits (402, 404, 406). A retraction button (524) is mounted to a casing of vacuum control module (500) and is operable to release the ratchet assembly to retract conduits (402, 404, 406). In addition, or in the alternative, spools (522) may be coupled to hand cranks (not shown) to manually retract conduits (402, 404, 406) about spools (522). In some versions, retraction button (524) is operated from biopsy device (100), for example, by a button (228) on notched upper control unit (220), such that a user can retract conduits (402, 404, 406) while using the device. By way of example only, a button (not shown) on biopsy device (100) may activate a solenoid to release the ratchet assembly. Accordingly, the user can reduce the amount of potential tangling and/or any excess conduit (402, 404, 406) around where the user is using biopsy device (100). In addition, or in the alternative, such remote retraction may be selectively braked or controlled (either by a brake or a motor) to slowly retract the conduit (402, 404, 406). Such slowed retraction may prevent conduit (402, 404, 406) from rapidly retracting and pulling biopsy device (100) out of the user's hands.

While conduits (402, 404, 406) are shown as separate conduits, it should be understood that conduits (402, 404, 406) may be combined into a single tube subdivided into any number of suitable conduits. In some versions, conduits (402, 404, 406) may be longitudinally fused together to form a rectangular unitary three conduit tube. Of course still further configurations for conduits (402, 404, 406) will be apparent to one of ordinary skill in the art in view of the teachings herein. In some versions conduits (402, 404, 406) may not retract, or only part of conduits (402, 404, 406) may retract. In such a configuration, conduits (402, 404, 406) may be separable from a connector (not shown) operable to couple to one or more receptacles (not shown) on vacuum control module (500). Accordingly, after conduits (402, 404, 406) are used in a procedure, conduits (402, 404, 406) may be detached from the connector and disposed of. New conduits (402, 404, 406) may be coupled to the connector for the next procedure. In one merely exemplary configuration, a reusable conduit portion may be coupled to a disposable conduit portion. The reusable conduit portion of this example may be coupled to the retraction system (520). Accordingly, the reusable conduit portion may have a predetermined size, such as five feet, and one or more disposable conduits may be coupled to the reusable conduit portion to provide various lengths of conduit for a procedure. When the procedure is finished, the disposable conduit portions are disposed of and the reusable conduit portion is retracted into vacuum control module (500) for storage. In addition, or in the alternative, retraction system (520) and conduits (402, 404, 406) may be constructed as a selectively insertable device that may be inserted or removed from vacuum control module (500). By way of example only, such a selectively insertable retraction system (520) may be configured similarly to the vacuum canisters described in U.S. Pat. No. 7,938,786, entitled "Vacuum Timing Algorithm for Biopsy Device," issued May 10, 2011 the disclosure of which is incorporated by reference herein. Accordingly, in some versions the entire retraction system (520) may be disposable or, in some versions, reclaimable to be resterilized for reuse.

In the present example, a power cord (420) extends from vacuum control unit (500) to electrically couple and power biopsy device (100). Power cord (420) may be configured to supply DC or AC power to biopsy device (100). In addition, or in the alternative, power cord (420) may also be operable to transmit data between vacuum control module (500) and biopsy device (100). Power cord (420) includes an end connector (not shown) configured to selectively couple to an end connector (298) of cable (290), shown in FIGS. 2-6. Accordingly, power cord (420) of vacuum control module (500) may be separable from holster (202) such that each may be stored separately, though this is merely optional. Power cord (420) of the present example is also coupled to a spring-loaded spool (522) that may be retracted by retraction system (520) described above. It should be understood that spool (522) to which power cord (420) is coupled may be a separate spool from the spools for conduits (402, 404, 406). In addition, the retraction system (520) for spool (522) to which power cord (420) is coupled may be a separate retraction system as well. For instance, vacuum control module (500) may have a removable retraction system (520) for conduits (402, 404, 406) that may be removed and disposed of while a permanent retraction system (520) is provided for power cord (420). Of course, some versions of biopsy device (100) may be internally powered such that power cord (420) may be omitted. In some versions, spools (522) may comprise a single spool having multiple discrete spools such that conduits (402, 404, 406) and power cord (420) are retracted and extended at the same time and rate. In some versions, power cord (420) may be incorporated into the singular tube conduit described above such that a single cord, having three subdivisions for fluid flow and one subdivision to transmit power, extends from vacuum control unit (500). Still further configurations for power cord (420), vacuum control module (500), and/or retraction systems (520) will be apparent to one of ordinary skill in the art in view of the teachings herein.

B. Exemplary Biopsy Device Overview

Biopsy device (100) of the present example is configured to be held by a user and inserted in a patient under guidance from an ultrasound imaging device. Of course, biopsy device (100) may instead be used under stereotactic guidance, MRI guidance, PEM guidance, BSGI guidance, or otherwise. It should also be understood that biopsy device (100) may be sized and configured such that biopsy device (100) may be operated by a single hand of a user. In particular, a user may grasp biopsy device (100), insert needle (110) into a patient's breast, and collect one or a plurality of tissue samples from within the patient's breast, all with just using a single hand. Alternatively, a user may grasp biopsy device (100) with more than one hand and/or with any desired assistance. In some settings, the user may capture a plurality of tissue samples with just a single insertion of needle (110) into the patient's breast. Such tissue samples may be pneumatically deposited in tissue sample holder (302), and later retrieved from tissue sample holder (302) for analysis. While examples described herein often refer to the acquisition of biopsy samples from a patient's breast, it should be understood that biopsy device (100) may be used in a variety of other procedures for a variety of other purposes and in a variety of other parts of a patient's anatomy (e.g., prostate, thyroid, etc.). Various exemplary components, features, configurations, and operabilities of biopsy device (100) will be described in greater detail below; while other suitable components, features, configurations, and operabilities will be apparent to those of ordinary skill in the art in view of the teachings herein.

Biopsy device (100) of the present example comprises a separable probe (102) and holster (202) as shown in FIGS. 2-6. In the present example, probe (102) is configured to initially slide onto holster (202) laterally until a distal probe portion (120) enters and abuts a portion of notched upper control unit (220), then probe (102) is slid distally to secure probe (102) to holster (202). Once slid distally, latch (190) of probe (102) engages a latch recess (238) of holster (202) to securely couple probe (102) to holster (202). Tissue may then be severed and transported proximally into tissue sample holder (302). Biopsy device (100) and tissue sample holder (302) may be further constructed in accordance with at least some of the teachings of U.S. Pat. No. 7,938,786, entitled "Vacuum Timing Algorithm for Biopsy Device," issued May 10, 2011; U.S. Pat. Pub. No. 2008/0221480, entitled "Biopsy Sample Storage," published Sep. 11, 2008; U.S. Pat. Pub. No. 2010/0317997, entitled "Tetherless Biopsy Device with Reusable Portion," published Dec. 16, 2010; U.S. Non-Provisional patent application Ser. No. 12/953,715, entitled "Handheld Biopsy Device with Needle Firing," filed Nov. 24, 2010; U.S. Non-Provisional patent application Ser. No. 13/086,567, entitled "Biopsy Device with Motorized Needle Firing," filed Apr. 14, 2011; U.S. Non-Provisional patent application Ser. No. 13/205,189, entitled "Access Chamber and Markers for Biopsy Device," filed Aug. 8, 2011; and/or U.S. Provisional Patent App. No. 61/727,889, entitled "Biopsy System with Graphical User Interface," filed Nov. 19, 2012, the disclosures of which are incorporated by reference herein. Of course still further configurations for biopsy system (10) will be apparent to one of ordinary skill in the art in view of the teachings herein.

II. Exemplary Holster

Holster (202) comprises a top housing cover (210), a housing base (260), and a cable (290). Cable (290) comprises a plurality of wires (292), shown in FIG. 6, to provide power and/or control signals to various components contained within housing base (260). Cable (290) further includes an end connector (298) operable to selectively couple holster (202) to a connector of power cord (420), described above, or, in some versions, end connector (298) may be directly coupleable to vacuum control module (500). Housing base (260) comprises a biocompatible rigid plastic material, such as polycarbonate, that is molded to include a distal upwardly bending arcuate portion (262), shown in FIGS. 2-4 and 17, such that housing base (260) may be positioned closer to a patient's body during use. By way of example only, arcuate portion (262) is sized to permit a portion of a patient's anatomy, such as a breast or other part of the patient's thorax, to at least partially occupy the curved cavity formed by arcuate portion (262) such that biopsy device (100) may be readily positioned at various orientations near to the patient's body. The configuration of arcuate portion (262) may permit greater access to a patient's breast than might otherwise be provided by a generally rectangular or cylindrical shaped biopsy device. Arcuate portion (262) extends proximally for approximately one-fifth the length of holster (202), though this is merely optional. In some versions, arcuate portion (262) may extend proximally for approximately half, less than half, or more than half of the longitudinal length of holster (202). In addition, or in the alternative, arcuate portion (262) may comprise a padded portion (not shown), such as a gauze pad, to reduce the "mechanical" feel of arcuate portion (262) in the event that arcuate portion (262) comes into contact with the patient's skin. Still further arrangements for arcuate portion (262) will be apparent to one of ordinary skill in the art in view of the teachings herein.

Figure 3:
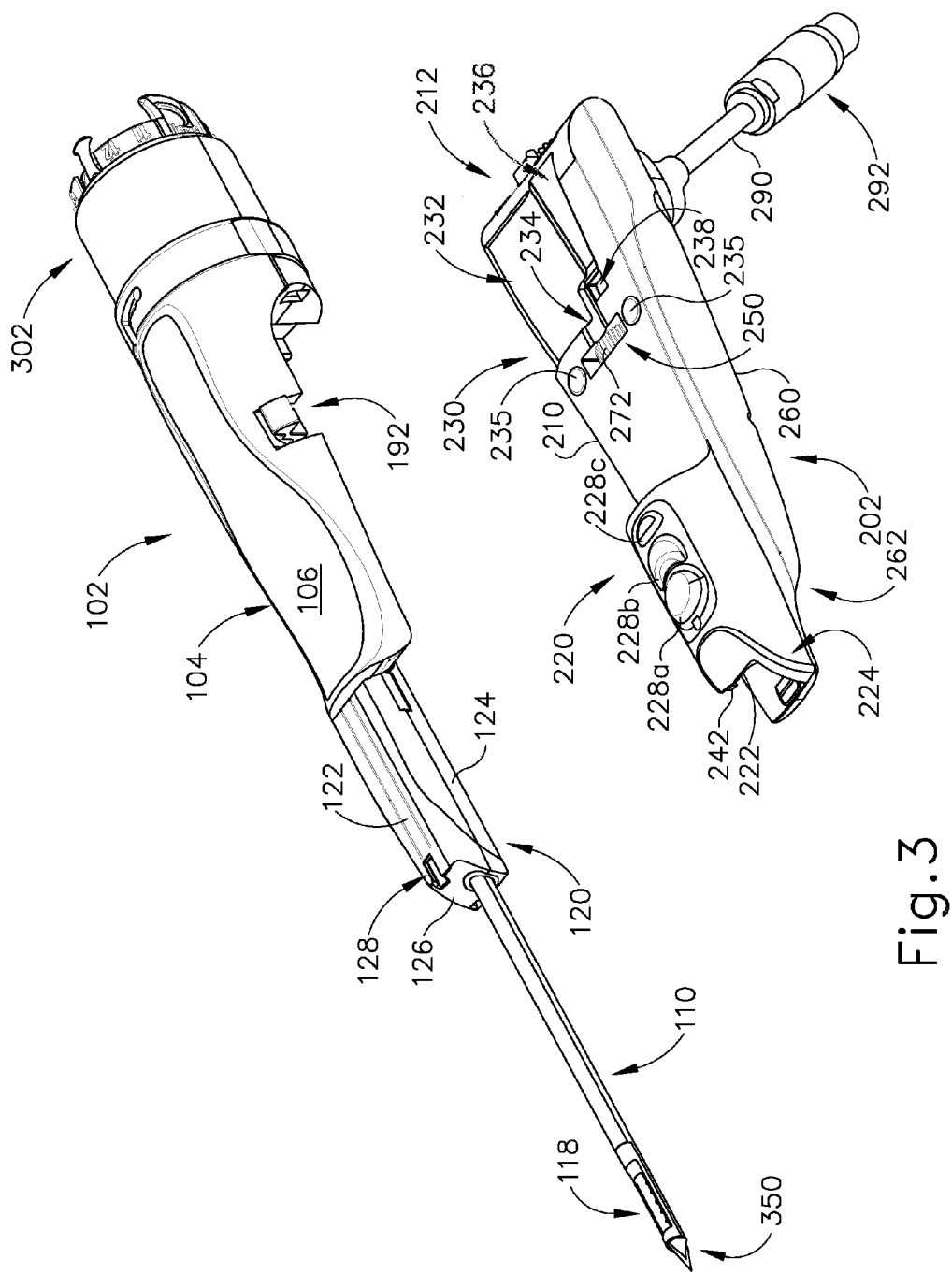
FIG. 3 depicts a perspective view of the biopsy device of FIG. 2 showing an exemplary probe decoupled from an exemplary holster.
Figure 4:
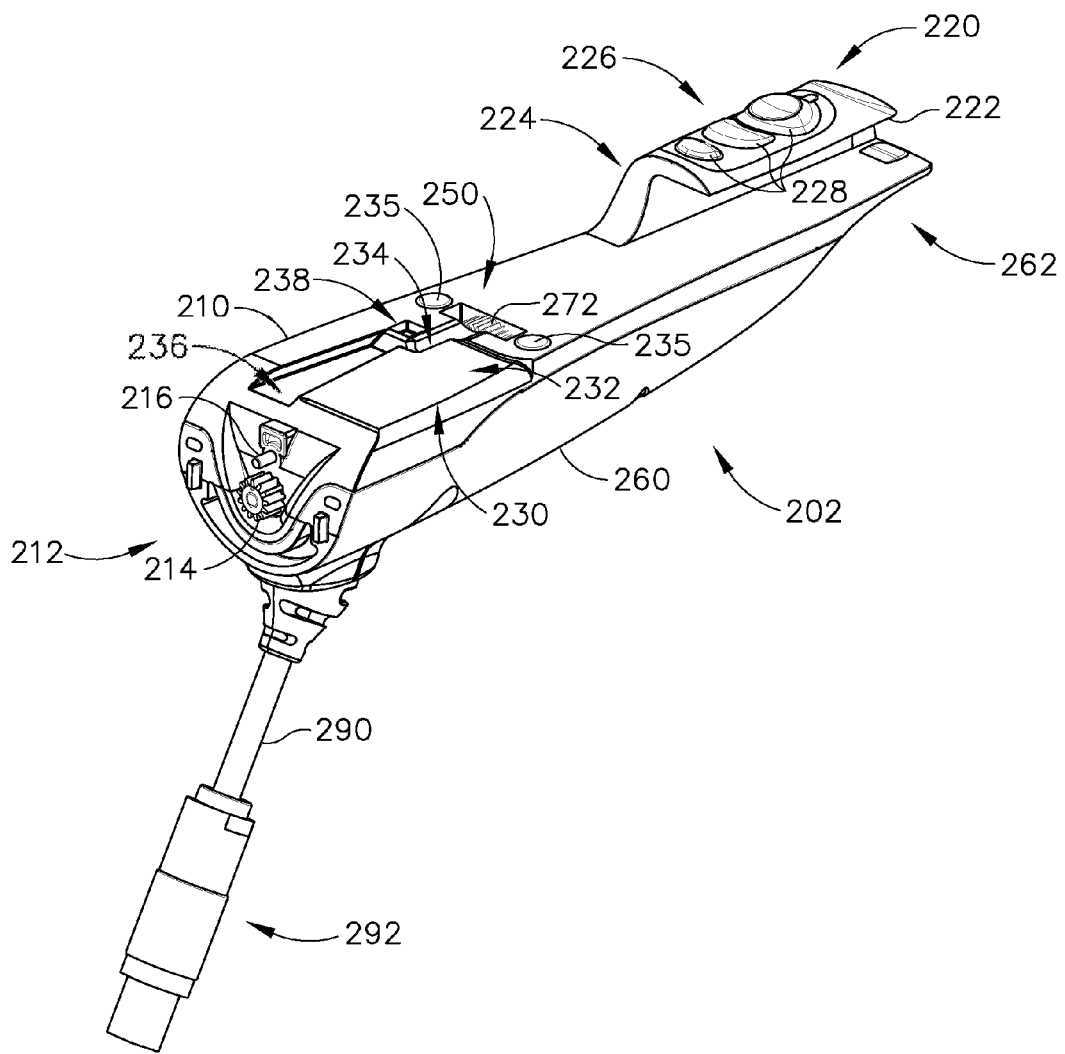
FIG. 4 depicts a rear perspective view of the holster of FIG. 3.

Referring now to FIGS. 3-4, top housing cover (210) also is formed of a biocompatible rigid plastic material, such as polycarbonate, and includes a notched upper control unit (220), a gear slot (230), a front rail (242), a latch recess (238), and a gear aperture (250). As best seen in FIG. 3, holster gear (272) is exposed through gear aperture (250) and is configured to mesh with probe gear (170) of probe (102) when probe (102) is coupled to holster (202). Accordingly, rotation of holster gear (272) rotates probe gear (170) to drive a cutter actuation assembly (150) in probe (102), described in greater detail below. Protrusions (235) are positioned on each side of gear aperture (250) and correspond to recesses (135) on probe (102). Gear slot (230) is a recessed portion of top housing cover (210) configured to permit probe gear (170) to travel along gear slot (230) as probe (102) is slid onto holster (202). Gear slot (230) comprises a lateral portion (232) and a longitudinal portion (234).

Probe (102) may be coupled to holster (202) by lateral loading and/or longitudinal loading. For lateral loading, probe (102) is initially positioned lateral to holster (202) and is then moved laterally toward holster (202). Probe gear (170) first enters lateral portion (232) and travels along lateral portion (232) until probe (102) is substantially longitudinally aligned with holster (202). Latch (190) of probe (102) also travels along lateral portion (232) during this initial lateral movement of a lateral loading operation. Once probe (102) is laterally positioned to the point where probe (102) is longitudinally aligned with holster (202), latch (190) is positioned in channel (236) and probe (102) is pushed longitudinally forward by the user (and/or holster (202) is pulled proximally by the user), causing probe gear (170) to travel within longitudinal portion (234) of gear slot (230) until probe gear (170) meshes with holster gear (272). Latch (190) of probe (102) also inserts within latch recess (238) of holster (202) when probe gear (170) meshes with holster gear (272). At this stage, probe (102) and holster (202) are fully coupled.

Alternatively, probe (102) may be coupled longitudinally to holster (202) by first positioning probe (102) proximal to holster (202) to longitudinally align probe (102) with holster (202). The user may push probe (102) forward (and/or pull holster (202) proximally) such that probe gear (170) enters lateral portion (232) and travels distally along lateral portion (232) to enter longitudinal portion (234) of gear slot (230) until probe gear (170) meshes with holster gear (272). Latch (190) directly enters channel (236) without first entering lateral portion (232) and slides within channel (236) of holster (202) as probe (102) is slid distally until latch (190) inserts within latch recess (238). Of course gear slot (230) is merely optional and may be omitted. In addition, or in the alternative, a similar gear slot (not shown) may be formed on a bottom portion of probe (102).

Regardless of whether probe (102) and holster (202) are coupled together through lateral loading or longitudinal loading, protrusions (235) of holster (202) insert within recesses (135) of probe (102) when probe gear (170) meshes with holster gear (272). This ensures that probe gear (170) is centrally aligned with holster gear (272). In addition, protrusions (235) act as rigid stand-offs, providing a consistent distance between the axis of probe gear (270) and the axis of holster gear (272) when probe (102) and holster (202) are coupled together. In some versions of biopsy device (100), plastic housing components of biopsy device (100) may deform slightly when a user grasps biopsy device (100) during use, particularly if the user squeezes probe (102) and holster (202) together substantially. In some such versions of biopsy device (100) that lack protrusions, such squeezing may drive probe gear (170) further into holster gear (272), reducing the distance between the axes of gears (170, 272), and creating increased friction and/or strain on the drive components. Protrusions (235) and recesses (135) may be formed by reinforcing material and may thereby substantially prevent such effects from occurring during normal use of biopsy device (100), by preventing general housing deformation from driving probe gear (170) into holster gear (272).

Also regardless of whether probe (102) and holster (202) are coupled together through lateral loading or longitudinal loading, as probe (102) is slid distally during the final stage of coupling with holster (202), a front slot (128) receives a front rail (242), which is best seen in FIG. 17 as being formed on the underside of upper control unit (220). The combination of front slot (128) and front rail (242) provide additional alignment for coupling probe (102) to holster (202). In addition, rail (242) may also be sized such that rail (242) resists lateral displacement of probe (102) relative to holster (202) once probe (102) is coupled to holster (202). Of course still further configuration for rail (242) and slot (128) will be apparent to one of ordinary skill in the art in view of the teachings herein.

Notched upper control unit (220) initially extends upwardly and then inwardly from a first surface of top cover (210), thereby forming an inverted L-shaped component having an overhang (222). In the example shown, notched upper control unit (220) comprises an upwardly extending portion (224) coupled to an overhang (222), thereby forming an upper boundary to secure probe (102) against holster (202). Accordingly, overhang (222) retains probe (102) against holster (202) even if biopsy device (100) is inverted or positioned in any other orientation. In addition, while notched upper control unit (220) increases the height of holster (202), it will be appreciated by one of ordinary skill in the art in view of the teachings herein that the width of holster (202) is narrowed by providing upper control unit (220). Accordingly, this narrowed width may permit a user to grasp holster (202) and/or the assembly biopsy device (100) in a similar manner to holding a pencil or other narrow-bodied object.

Notched upper control unit (220) further includes a control panel (226) having a plurality of buttons (228) thereon. In the present example, buttons (228) comprise a rocker button (228a), a first button (228b), and a second button (228c). In the present example, second button (228c) is operable to selectively activate biopsy device (100) to take a biopsy sample of tissue. First button (228b) is operable to selectively apply a vacuum from vacuum control module (500) to one or more portions of biopsy device (100), such as to cutter lumen (136). Rocker button (228a) is operable to selectively advance or retract cutter (152), thereby opening or closing lateral aperture (118). Buttons (228a, 228b, 228c) may of course have other uses, as will be apparent to one of ordinary skill in the art in view of the teachings herein. Moreover, additional buttons (228) may be provided to provide additional functionality. For instance, as noted above, one such additional button (228) may include a button to trigger retraction of conduits (402, 404, 406) and/or power cord (420) into vacuum control unit (500). In addition, or in the alternative, indicators (not shown) may be included on notched upper control unit (220) to provide visual feedback to the user. In yet a further configuration, notched upper control unit (220) may comprise a touch panel, such as a resistive touch screen, capacitive touch screen, piezoelectric touch screen, acoustic pulse recognition, and/or any other type of touch screen as will be apparent to one of ordinary skill in the art in view of the teachings herein. By way of example only, one or more of buttons (228) may be operable in accordance with at least some of the teachings of U.S. patent application Ser. No. 13/595,331, entitled "Multi-Button Biopsy Device," filed Aug. 27, 2012, the disclosure of which is incorporated by reference herein; and/or in a accordance with at least some of the teachings of U.S. Provisional Patent App. No. 61/727,889, entitled "Biopsy System with Graphical User Interface," filed Nov. 19, 2012, the disclosure of which is incorporated by reference herein.

Figure 15:
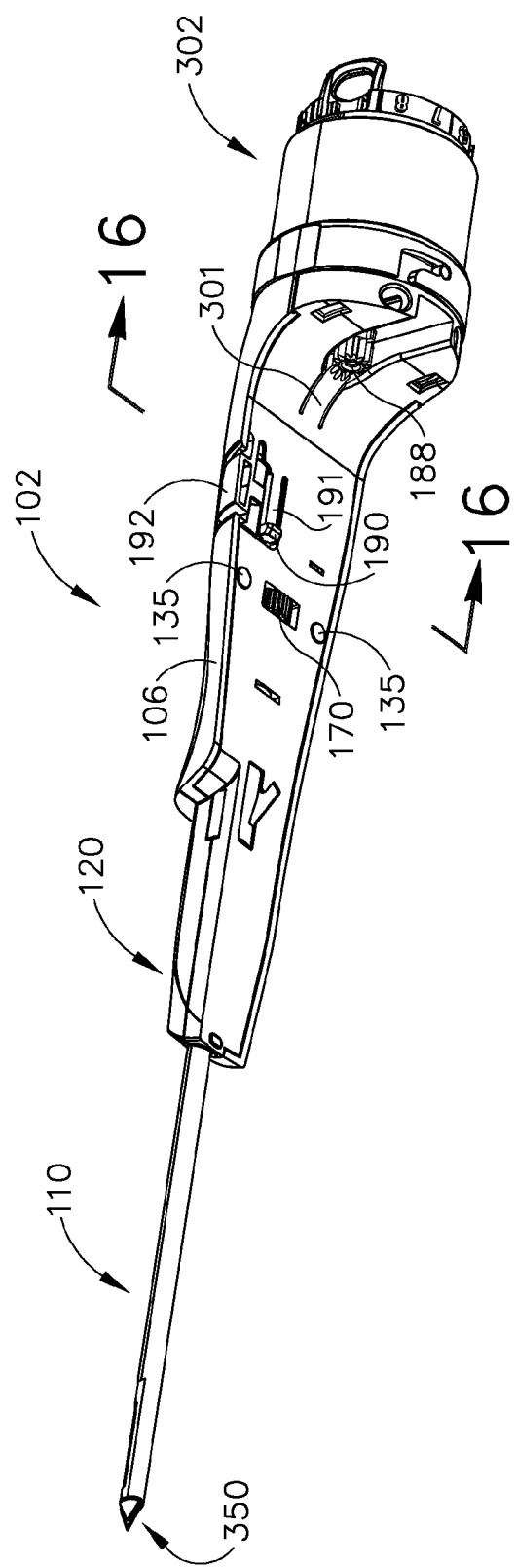
FIG. 15 depicts a bottom perspective view of the probe of FIG. 3.
Figure 16:
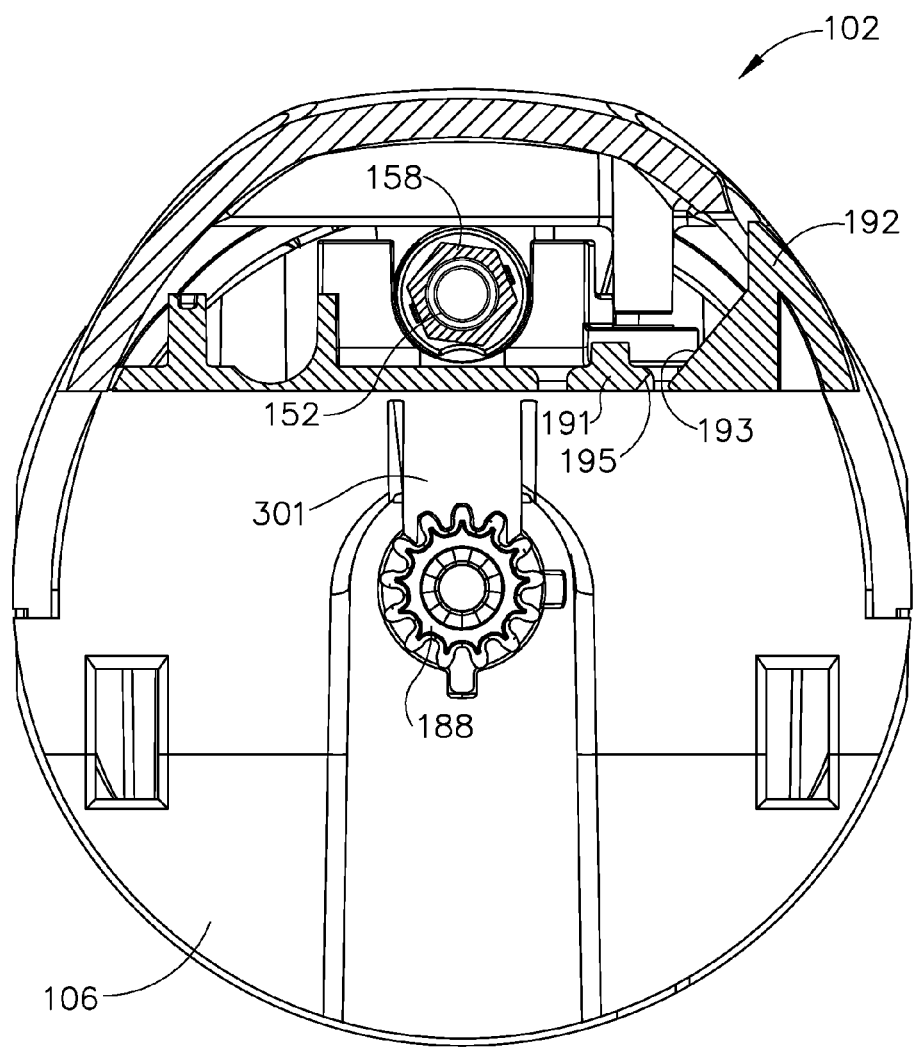
FIG. 16 depicts a front cross-sectional view of the probe of FIG. 3, taken along line 16-16 of FIG. 15.

As noted previously, latch (190) engages latch recess (238) to selectively couple probe (102) to holster (202). As best seen in FIGS. 15-16, latch (190) is positioned at the free end of a resilient arm (191), which resiliently biases latch (190) into latch recess (238) when probe (102) is fully seated with respect to holster (202). A latch release button (192) is positioned near latch (190), and is configured to disengage latch (190) from latch recess (238) when the operator wishes to decouple probe (102) from holster (202). In particular, latch release button (192) includes an integral cam ramp (193) that presents an upwardly sloped surface. When latch release button (192) is depressed, the resulting movement urges cam ramp (193) toward resilient arm (191). Cam ramp (193) thereby drives resilient arm (191) upwardly, which in turn pulls latch (190) out of engagement from recess (238).

The operator may then pull probe (102) proximally relative to holster (202) while continuing to depress release button (192), thereby decoupling probe (102) from holster (202). Of course, any other suitable structures and features may be used to decouple probe (102) from holster (202). Furthermore, in some versions biopsy device (100) may comprise a unitary construction that does not include a probe portion that may be decoupled from a holster portion.

Figure 14:
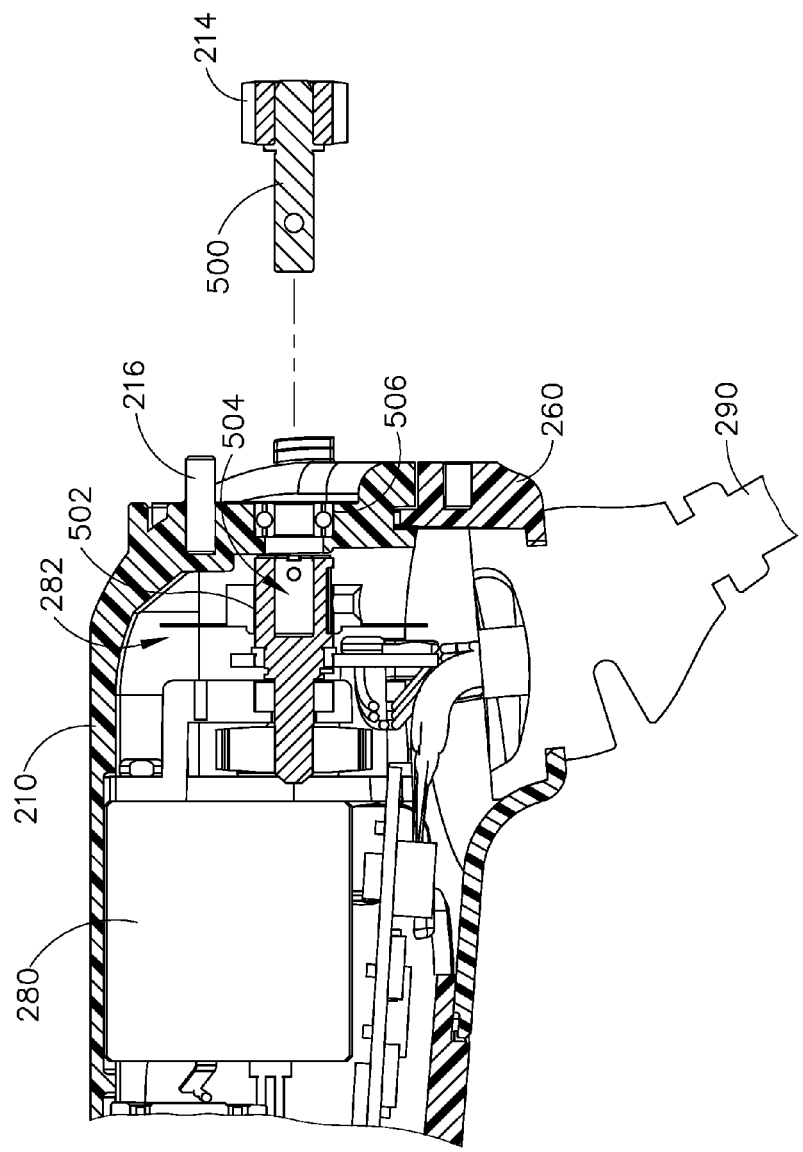
FIG. 14 depicts a partial, side, cross-sectional exploded view of a tissue sample holder drive shaft assembly.

Top cover (210) further includes a proximal end (212) having a sample holder cog (214) and a peg (216) extending proximally therefrom. Sample holder cog (214) is operable to rotate a rotatable manifold (310) of tissue sample holder (302) to rotate a plurality of tissue sample chambers into alignment with a cutter lumen (136), as will be discussed in more detail below. In the present example, as best seen in FIG. 14, sample holder cog (214) is secured to a shaft (500). Shaft (500) is coupled with a drive shaft (502) of motor (280). In particular, drive shaft (502) includes a socket (504) that is configured to receive shaft (500). A set screw and/or some other feature may be used to secure shaft (500) in socket (504). A rolling bearing (506) is secured to top cover (210) of holster (202) and supports shaft (500). It should be understood that providing shafts (500, 502) as separate components that are secured together may facilitate assembly of holster (202). In some other versions, shaft (502) extends through top cover (210) and cog (214) is secured directly to shaft (502). Other suitable components, features, and arrangements will be apparent to those of ordinary skill in the art in view of the teachings herein.

Peg (216) is operable to decouple a parking pawl (301) from a tissue sample holder gear (188) when probe (102) is coupled to holster (202). Parking pawl (301) and tissue sample holder gear (188) are best shown in FIGS. 15-16, in which parking pawl (301) is engaged with tissue sample holder gear (188) to selectively prevent rotation of a manifold (310) relative to probe (102). Sample holder cog (214), peg (216), and/or parking pawl (301) may be further constructed and/or configured in accordance with at least some of the teachings of U.S. Pat. No. 7,938,786, entitled "Vacuum Timing Algorithm for Biopsy Device," issued May 10, 2011 and/or U.S. Non-Provisional patent application Ser. No. 13/205,189, entitled "Access Chamber and Markers for Biopsy Device," filed Aug. 8, 2011, the disclosures of which are incorporated by reference herein.

Still further configurations for top cover (210) of holster (202) will be apparent to one of ordinary skill in the art in view of the teachings herein.

Figure 5:
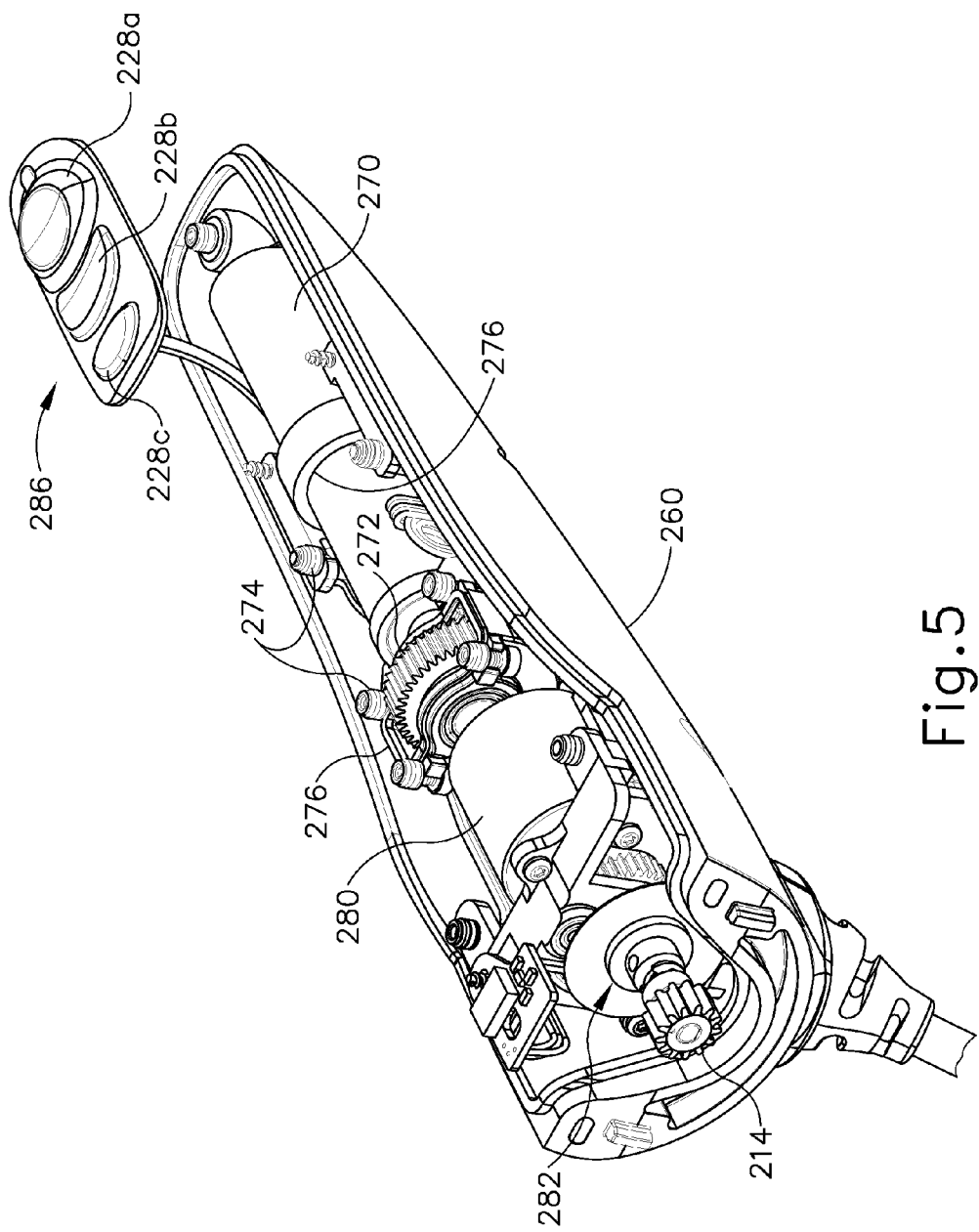
FIG. 5 depicts a rear perspective view of the holster of FIG. 3 with a top housing cover omitted.
Figure 6:
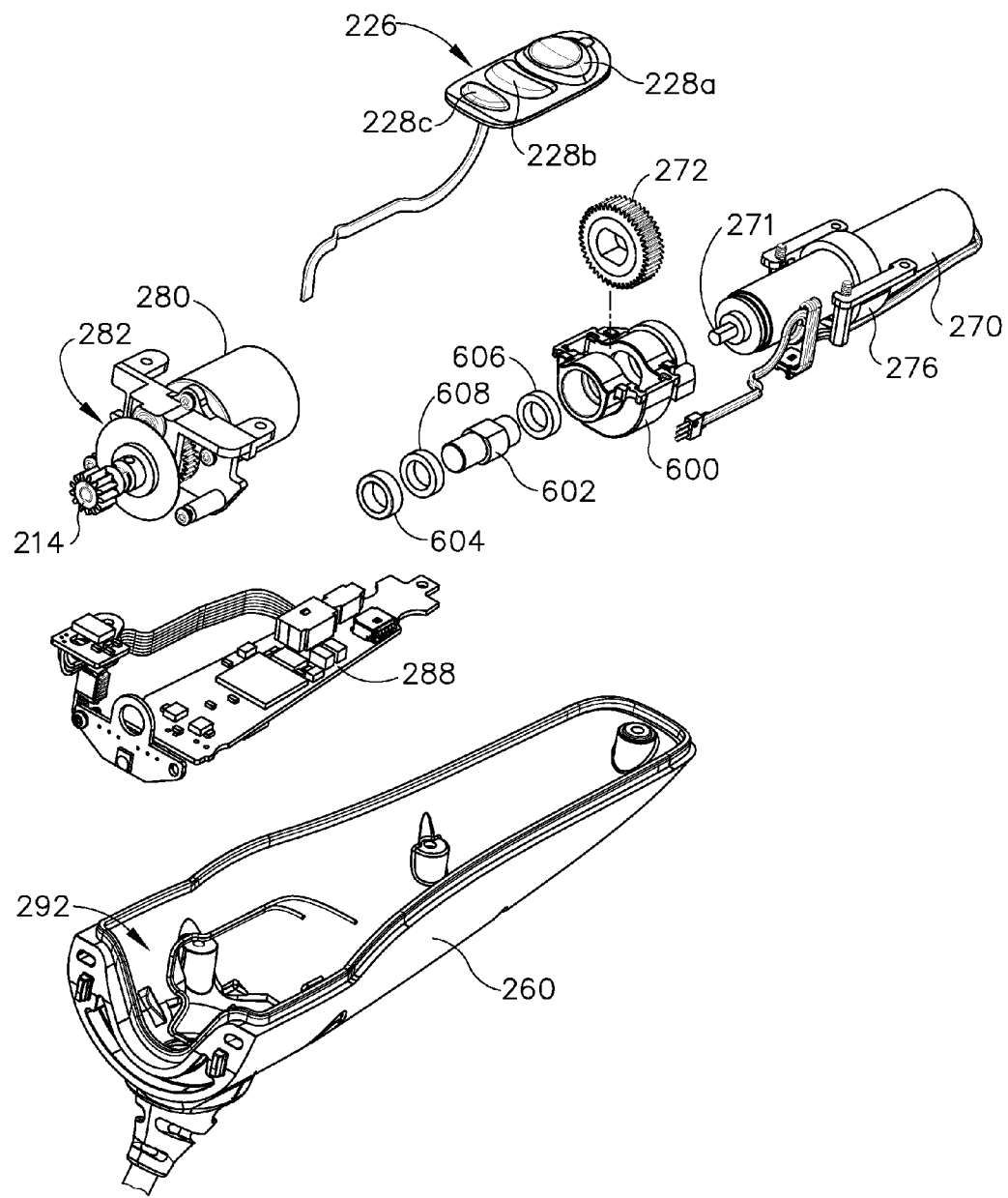
FIG. 6 depicts an exploded perspective view of the holster of FIG. 3.

FIGS. 5-6 depict holster (202) with top cover (210) removed, showing the components (270, 280, 288) contained within housing base (260). In the present example, holster (202) includes a cutter drive motor (270), a sample holder motor (280), and a controller (288). In the present example, cutter drive motor (270) is coupled to holster gear (272), a top portion of which extends out of top cover (210) through gear aperture (250). Cutter drive motor (270) is operable to engage and drive cutter actuation assembly (150) within probe (102), as will be discussed in greater detail below. In the present example, cutter drive motor (270) is mounted with one or more rubber bushings (274) and/or rubber gaskets (276) to isolate vibrations from cutter drive motor (270). Cutter drive motor (270) includes a drive shaft (271), which extends into a holster gear housing (600). Drive shaft (271) is coupled with an adapter shaft (602), which is disposed within holster gear (272). A rolling bearing (604) supports adapter shaft (602) in holster gear housing (600). A pair of spring energized seals (606, 608) are positioned coaxially about adapter shaft (602), with a distal seal (606) being positioned distal to holster gear (272) and a proximal seal (608) being positioned proximal to adapter shaft (602). Seals (606, 608) are configured to prevent fluid (e.g., saline, bodily fluid, etc.) from entering the interior of holster (202) via gear aperture (250). Of course, any other suitable features may be used to substantially seal the interior of holster (202).

Sample holder motor (280) is coupled to sample holder cog (214) and includes an encoder assembly (282) operable to transmit the rotational position of sample holder cog (214) to controller (288). Controller (288) of the present example is electrically coupled to cutter drive motor (270), sample holder motor (280), encoder assembly (282), control panel (226) and vacuum control module (500). Controller (288) is operable to output control signals to cutter drive motor (270) and/or sample holder motor (280) in response to one or more control or input signals from encoder assembly (282), control panel (226) and vacuum control module (500). Controller (288) may be further constructed or configured in accordance with at least some of the teachings of U.S. Pat. No. 7,938,786, entitled "Vacuum Timing Algorithm for Biopsy Device," issued May 10, 2011; U.S. Pat. Pub. No. 2010/0317997, entitled "Tetherless Biopsy Device with Reusable Portion," published Dec. 16, 2010; U.S. Non-Provisional patent application Ser. No. 12/953,715, entitled "Handheld Biopsy Device with Needle Firing," filed Nov. 24, 2010; U.S. Non-Provisional patent application Ser. No. 13/086,567, entitled "Biopsy Device with Motorized Needle Firing," filed Apr. 14, 2011; and/or U.S. Provisional Patent App. No. 61/727,889, entitled "Biopsy System with Graphical User Interface," filed Nov. 19, 2012, the disclosures of which are incorporated by reference herein.

Still further constructions and/or configurations for holster (202) will be apparent to one of ordinary skill in the art in view of the teachings herein.

III. Exemplary Probe

Figure 7:
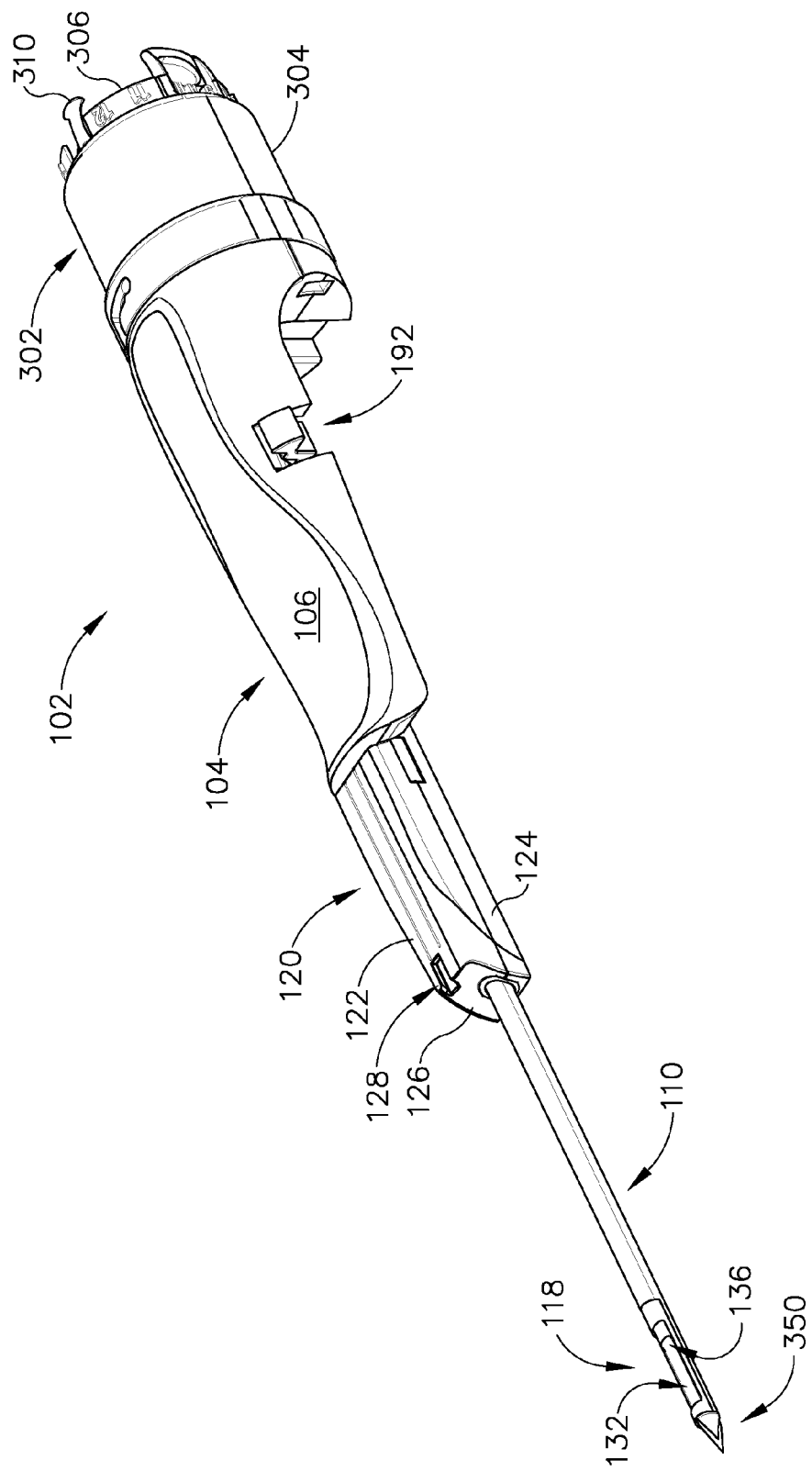
FIG. 7 depicts a perspective view of the probe of FIG. 3.

FIGS. 2-3 and 7-9 depict an exemplary probe (102) configured to couple to holster (202) described above. Probe (102) of the present example comprises a probe body (104), a needle (110) extending distally from probe body (104), and a tissue sample holder (302) detachably coupled to a proximal end of probe (102). Probe body (104) of the present example comprises a biocompatible rigid plastic material, such as polycarbonate, divided into a chassis portion and a top probe cover, though this is merely optional. Indeed, in some versions, probe body (104) may be of unitary construction. As shown in FIGS. 3 and 7, probe body (104) includes a main portion (106) and a distal probe portion (120). Main portion (106) includes a slot (128) configured to receive a rail (242) of top cover (210), as described above. Referring back to FIG. 15, latch (190) of the present example is integrally formed as part of main portion (106), though this is merely optional and latch (190) may comprise a separate component mechanically coupled to main portion (106). Other suitable configurations and/or constructions for main portion (106) and/or latch (190) will be apparent to one of ordinary skill in the art in view of the teachings herein.

Figure 2:
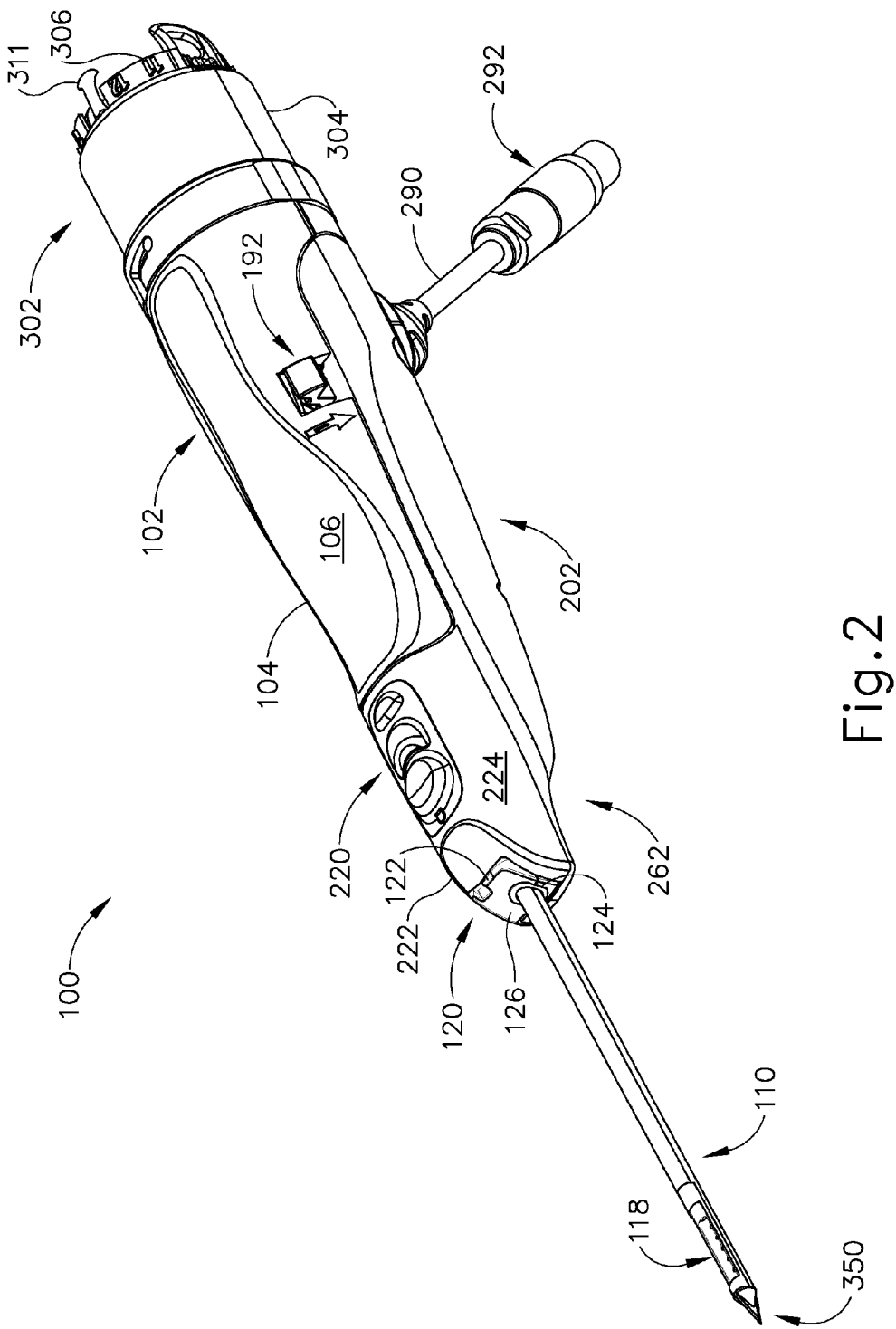
FIG. 2 depicts a perspective view of an exemplary biopsy device.

Distal probe portion (120) of the present example extends from main portion (106) and includes a top surface (122), a lateral surface (124), an outer surface (126), and a front slot (128). Top surface (122) and lateral surface (124) of the present example are formed substantially perpendicular to each other and are sized such that distal probe portion (120) nests beneath overhang (222) and adjacent to upwardly extending portion (224). Accordingly, as seen in FIG. 2, lateral surface (124) abuts upwardly extending portion (224) and top surface (122) is enclosed by overhang (222). Outer surface (126) of the present example is shaped to provide a smooth transition from distal probe portion (120) to notched upper control unit (220) when probe (102) is coupled to holster (202), though this is merely optional.

Figure 8:
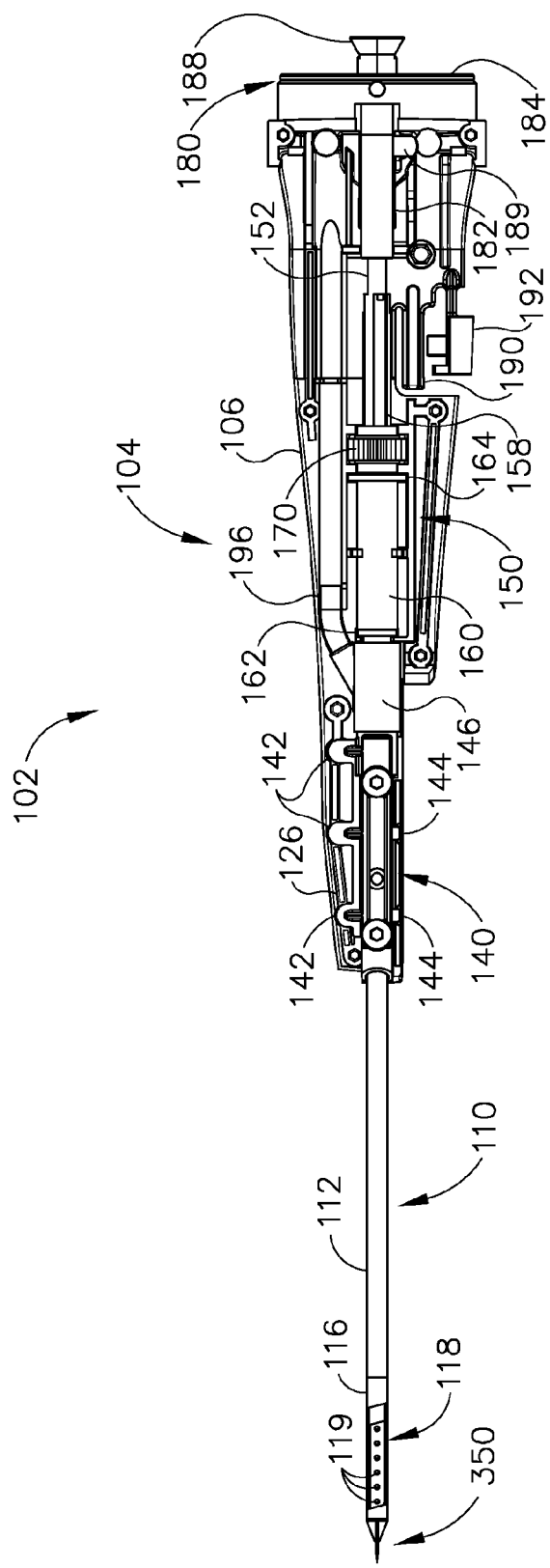
FIG. 8 depicts a top plan view of the probe of FIG. 3 with a top probe cover omitted.
Figure 9:
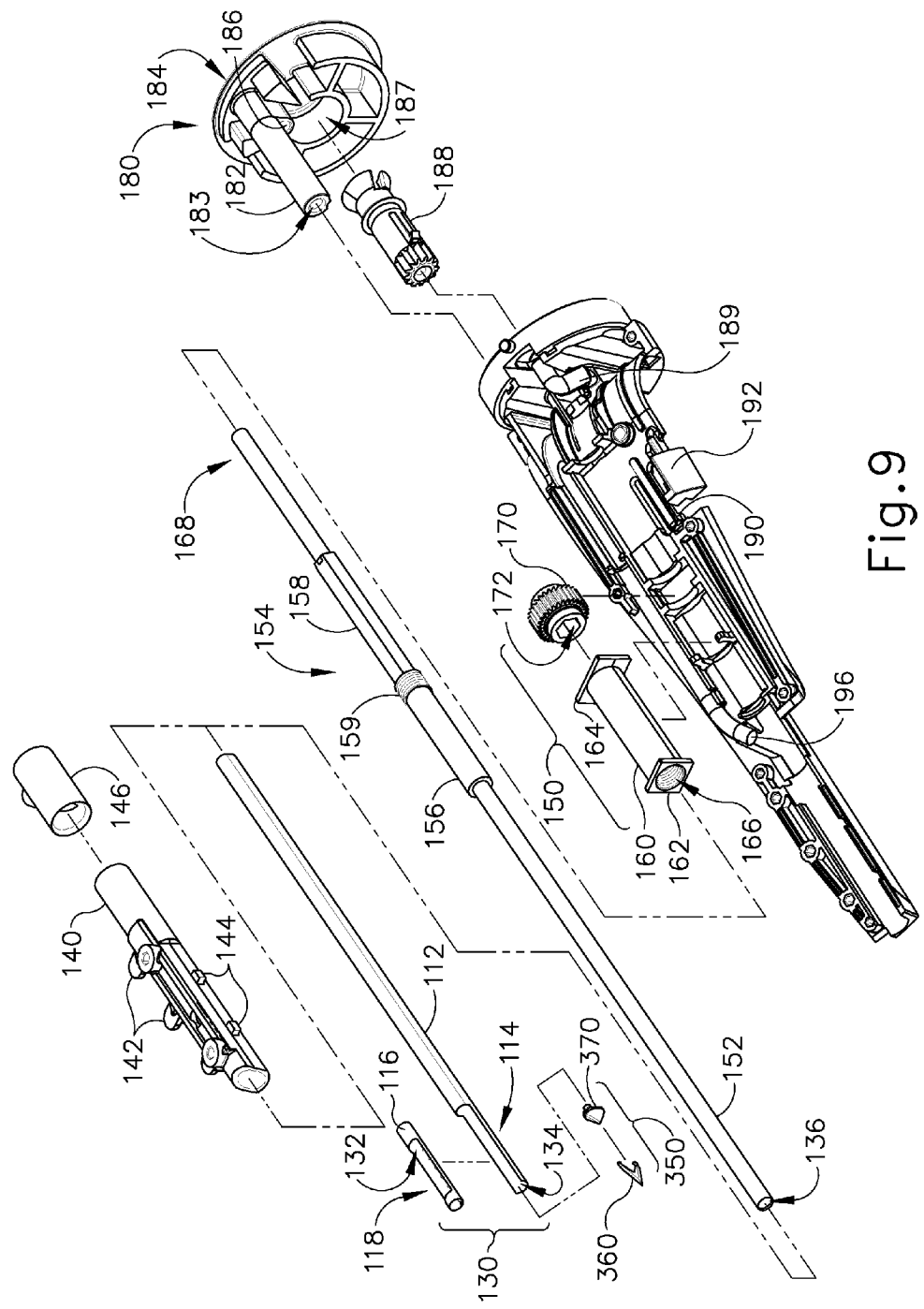
FIG. 9 depicts an exploded perspective view of the probe of FIG. 3.

Needle (110) is secured within probe body (104) by manifold (140), shown in FIGS. 8-9, and extends distally therefrom. Needle (110) terminates with blade assembly (350) coupled to distal end (130) of needle (110), as will be described in greater detail below. In the present example, needle (110) comprises an ovular two-piece needle having an ovular cannula tube (112), with a notch (114) formed at a distal end of ovular tube (112), and an insert (116). Notch (114) is sized to receive insert (116) such that insert (116) and ovular tube (112) are substantially flush at distal end (130) and form a two tiered needle having a first lumen (132) and a second lumen (134). In the present example, insert (116) comprises a cylindrical tube having a relatively large lateral aperture (118) and a relatively smaller set of lateral openings (119) formed in a sidewall of insert (116) opposite to lateral aperture (118). As will be apparent to one of ordinary skill in the art in view of the teachings herein, openings (119) allow fluid communication between second lumen (134) and first lumen (132). Needle (110) may be further constructed in accordance with at least some of the teachings of U.S. Non-Provisional patent application Ser. No. 13/150,950, entitled "Needle Assembly and Blade Assembly for Biopsy Device," filed Jun. 1, 2011 and/or in any other configuration as will be apparent to one of ordinary skill in the art in view of the teachings herein.

Manifold (140) of the present example receives needle (110) into an ovular aperture formed in manifold (140) to fixedly secure needle (110) into distal probe portion (120). While the present example depicts manifold (140) anchoring needle (110) within distal probe portion (120), it should be understood that manifold (140) may be anchored anywhere within probe (102). Manifold (140) further includes a plurality of hex tabs (142) and square tabs (144) to fixedly secure manifold (140) within distal probe portion (120). Hex tabs (142) include a hexagonal protrusion (not shown) extending from hex tabs (142) and configured to insert into complementary hex shaped recesses formed in distal probe portion (120) while the portion from which the hexagonal protrusions extend rests atop the framework within distal probe portion (120). Square tabs (144) insert into square recesses formed in distal probe portion (120). Accordingly, hex tabs (142) and square tabs (144) cooperatively secure manifold (140) within distal probe portion (120). It should be understood from the present example that manifold (140) substantially secures needle (110) to probe body (104) such that longer needles may be used with biopsy device (100) due to the anchoring provided by manifold (140). Of course it should be understood that manifold (140), hex tabs (142), and square tabs (144) are merely optional. By way of example only, tabs other than hex tabs (142) and/or square tabs (144) may be used, or, in some versions, manifold (140) may be integrally formed with distal probe portion (120) such that tabs (142, 144) may be omitted entirely. Still further configurations for manifold (140) will be apparent to one of ordinary skill in the art in view of the teachings herein.

In the example shown in FIGS. 8-9, a fluid junction member (146) is coupled to a proximal end of manifold (140) to fluidly couple second lumen (134) with one or more of conduits (400) described above. Fluid junction (146) is substantially sealed at a proximal end by distal sealing cylinder (156) of cutter overmold (154), as will be described below. Cutter (152) is inserted into insert (116) such that first lumen (132) is substantially fluidly coupled and sealed with cutter (152) and cutter lumen (136). Accordingly, the portion of ovular tube (112) extending proximally from insert (116) fluidly couples second lumen (134) to manifold (140) and fluid junction member (146). As seen in FIGS. 8-9, fluid junction (146) includes a Y-joint that couples fluid junction (146) to an inlet tube (196) that is subsequently coupled to one or more conduits (400), described above. By way of example only, inlet tube (196) may be selectively fluidly coupled to a vacuum source, a saline source, and/or an atmospheric source to selectively supply vacuum, saline, and/or atmospheric air through second lumen (134). Such selective supply of vacuum, saline, and/or atmospheric air may be controlled by vacuum control module (500) and/or through other valving assemblies, as will be apparent to one of ordinary skill in the art in view of the teachings herein. It should be understood that valving assemblies and/or vacuum systems may be provided in accordance with at least some of the teachings of U.S. Pat. No. 7,854,706, entitled "Clutch and Valving System for Tetherless Biopsy Device," issued Dec. 1, 2010, the disclosure of which is incorporated by reference herein; U.S. Pat. No. 7,938,786, entitled "Vacuum Timing Algorithm for Biopsy Device," issued May 10, 2011, the disclosure of which is incorporated by reference herein; U.S. Provisional Patent App. No. 61/598,939, entitled "Biopsy Device Valve Assembly," filed Feb. 15, 2012, the disclosure of which is incorporated by reference herein; and/or otherwise.

As noted above, cutter (152) is inserted into insert (116) to fluidly couple cutter lumen (136) with first lumen (132). A proximal end (168) of cutter (152) is also fluidly coupled to connector tube (182) of tissue sample holder seal (180), as will be described below, thereby providing a fluid passageway for tissue to travel from first lumen (132) into tissue sample holder (302). In the present example, cutter (152) comprises an elongate tubular member having a honed distal end operable to sever tissue as cutter (152) is advanced distally within insert (116). Accordingly, when tissue is prolapsed into lateral aperture (118) (such as by providing a vacuum through second lumen (134)) cutter (152) may be advanced by cutter actuation assembly (150) to sever the tissue. A vacuum may then be applied through tissue sample holder (302) to draw the tissue proximally through cutter lumen (136) and into a sample holder of a tissue sample tray (306) (shown in FIGS. 2, 7, and 10). Thus, tissue may be harvested from a location proximate to lateral aperture (118) and deposited within tissue sample holder (302). Of course tissue may be deposited at other locations, as will be apparent to one of ordinary skill in the art in view of the teachings herein.

Cutter (152) of the present example includes a unitary cutter overmold (154) that is operable to rotate and translate cutter (152) within needle (110). In the present example, cutter overmold (154) is formed of plastic molded about cutter (152) to fixedly secure cutter overmold (154) to cutter (152), though any other suitable materials may be used, and cutter overmold (154) may be secured relative to cutter (152) using any other suitable structures or techniques (e.g., set screws, etc.). Cutter overmold (154) comprises a distal sealing cylinder (156), a proximal hex end (158), and threading (159) interposed therebetween. As noted above, distal sealing cylinder (156) is inserted into fluid junction (146) to fluidly seal the proximal end of fluid junction (146). In some versions, an o-ring (not shown) or other gasket (not shown) may be disposed about distal sealing cylinder (156) to assist in fluidly sealing the proximal end of fluid junction (146). Of course other configurations for distal sealing cylinder (156) and/or components to seal the proximal end of fluid junction (146) will be apparent to one of ordinary skill in the art in view of the teachings herein.

Threading (159) of cutter overmold (154) is configured to engage and thread into internal threading (166) of nut member (160). In the present example, nut member (160) is fixedly secured relative to probe (102) such that rotation of cutter (152) engages threading (159) and internal threading (166) to longitudinally advance or retract cutter (152) relative to needle (110) and probe (102) when cutter (152) is rotated. For instance, as shown in FIGS. 8-9, nut member (160) comprises a distal square end (162) and a proximal square end (164), each of which anchors nut member (160) to probe (102) such that nut member (160) does not rotate or translate relative to probe (102). Of course it should be understood that in some versions nut member (160) may be integrally formed or otherwise affixed to probe (102). By way of example only, threading (159, 166) may be configured to have a pitch that provides approximately 40-50 threads per inch. Such a thread pitch may provide a ratio of cutter (152) rotation to cutter (152) translation that is ideal for severing tissue. Alternatively, any other thread pitch may be used. Still further configurations of nut member (160) will be apparent to one of ordinary skill in the art in view of the teachings herein.

Cutter overmold (154) also includes a proximal hex end (158) configured to insert into and engage with hex recess (172) formed through probe gear (170). Accordingly, when probe gear (170) is rotated, the proximal hex end (158) is rotated. This rotation causes threading (159) to engage internal threading (166) of nut member (160), thereby actuating cutter (152) proximally or distally depending upon the rotation direction of probe gear (170). As noted above, probe gear (170) extends out of the bottom of probe (102) and is configured to mesh with holster gear (272). When probe (102) is coupled to holster (202), cutter drive motor (270), described above, is operable to drive cutter (152) to actuate proximally or distally as threading (159) threads within nut member (160). Hex end (158) is further configured such that cutter (152) and cutter overmold (154) may translate longitudinally relative to probe gear (170) while probe gear (170) is still operable to rotate cutter (152) and cutter overmold (154). Accordingly, probe gear (170) remains engaged with holster gear (272) while cutter (152) and cutter overmold (154) actuate longitudinally. Of course it should be understood that proximal hex end (158) and hex recess (172) are merely optional and may comprise any other complementary features that mesh to transfer rotational movement, including stars, splines, squares, triangles, etc.

Figure 10:
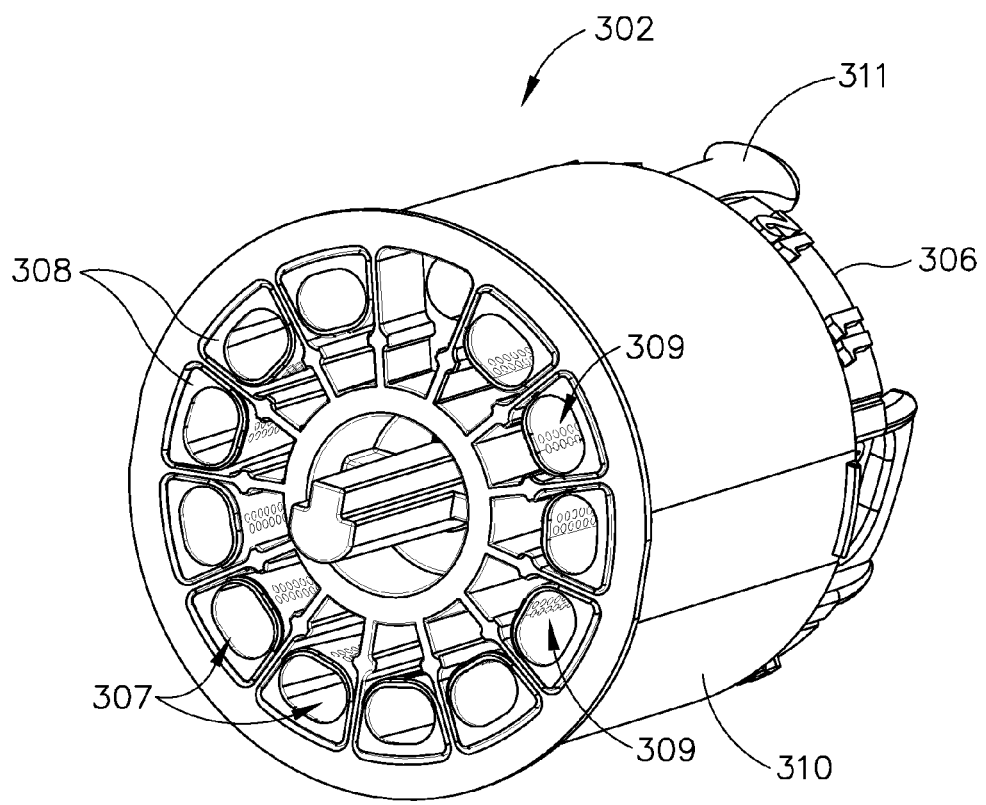
FIG. 10 depicts a perspective view of an exemplary tissue sample holder.

Tissue sample holder (302), shown in FIG. 10, is coupled to a proximal end of probe (102) and is fluidly coupled to cutter (152) such that tissue samples are transported proximally through cutter lumen (136) and into a sample holding chamber of tissue sample trays (306). Tissue sample holder (302) may be constructed in accordance with at least some of the teachings of U.S. Pat. No. 7,938,786, entitled "Vacuum Timing Algorithm for Biopsy Device," issued May 10, 2011; U.S. Pat. Pub. No. 2008/0221480, entitled "Biopsy Sample Storage," published Sep. 11, 2008; U.S. Non-Provisional patent application Ser. No. 13/205,189, entitled "Access Chamber and Markers for Biopsy Device," filed Aug. 8, 2011; U.S. Non-Provisional patent application Ser. No. 13/218,656, entitled "Biopsy Device Tissue Sample Holder with Bulk Chamber and Pathology Chamber," filed Aug. 26, 2011; U.S. Provisional Patent App. No. 61/727,889, entitled "Biopsy System with Graphical User Interface," filed Nov. 19, 2012; and/or otherwise.

Tissue sample holder (302) of the present example comprises a cover (304) containing a rotatable manifold (310) with a plurality of tissue sample trays (306) inserted into rotatable manifold (310). Rotatable manifold (310) comprises a plurality of longitudinal chambers extending therethrough and annularly disposed about rotatable manifold (310). Accordingly, each chamber can be selectively aligned with cutter (152) and connector tube (182), described below, such that tissue samples can be transported from lateral aperture (118) into each chamber. Each chamber comprises an upper longitudinal tray portion and a lower fluid portion that is parallel and offset from the upper tray portion. Merely exemplary chambers are shown and described in U.S. Pat. Pub. No. 2008/0221480, entitled "Biopsy Sample Storage," published Sep. 11, 2008, the disclosure of which is incorporated by reference herein; U.S. Non-Provisional patent application Ser. No. 13/205,189, entitled "Access Chamber and Markers for Biopsy Device," filed Aug. 8, 2011, the disclosure of which is incorporated by reference herein; U.S. Non-Provisional patent application Ser. No. 13/218,656, entitled "Biopsy Device Tissue Sample Holder with Bulk Chamber and Pathology Chamber," filed Aug. 26, 2011, the disclosure of which is incorporated by reference herein; and U.S. Provisional Patent App. No. 61/727,889, entitled "Biopsy System with Graphical User Interface," filed Nov. 19, 2012, the disclosure of which is incorporated by reference herein.

The tray portion is configured to receive a sample holder (308) of tissue sample trays (306) such that sample holder (308) is configured to receive a severed tissue sample therein. Each sample holder (308) of tissue sample trays (306) comprises a floor, a pair of sidewalls, and a proximal wall forming a compartment (307) that is configured to receive a tissue sample therein. The floor, sidewalls, and/or proximal wall include a plurality of holes (309) such that fluid may be communicated from within each sample holder (308) to the lower portion of the corresponding chamber formed in the rotatable manifold. When a vacuum is applied to the lower fluid portion, the vacuum is transmitted through sample holder (308), through connector tube (182), into cutter (152) and to lateral aperture (118). Accordingly, when the vacuum is applied, a severed tissue sample is transported proximally by the vacuum into a corresponding sample holder (308). Of course other configurations for tissue sample holder (302) will be apparent to one of ordinary skill in the art in view of the teachings herein. In some versions, tissue sample trays (306) and/or sample holders (308) comprise a high-contrast color compared to the color of the tissue samples, for instance, green, red, blue, etc., such that a user may visually detect the presence of a tissue sample within tissue sample trays (306). In the example shown, a dedicated passage does not receive a sample holder (308); instead, a plug (311) is provided to selectively seal a dedicated passage.

Referring back to FIG. 9, tissue sample holder (302) is coupled to cutter (152) by a tissue sample holder seal (180). Seal (180) comprises a proximal wall (184) formed as a disk that is configured to seal a distal end of tissue sample holder (302) to a proximal end of probe (102). By way of example only, proximal wall (184) may comprise a resilient silicon rubber disk against which tissue sample holder (302) may be compressed to form a fluid-tight seal. In some versions, proximal wall (184) may include an annular recess (not shown) sized to receive and form an interference or compression fit with a distal rim of tissue sample holder (302) to further seal tissue sample holder (302) to seal (180). Tissue sample holder seal (180) of the present example also includes a connector tube (182) that extends distally into probe (102) to fluidly couple to proximal end (168) of cutter (152). Connector tube (182) is integrally formed with a proximal wall (184) and includes an internal passageway (183) into which proximal end (168) of cutter (152) is inserted. In the example shown, connector tube (182) has a sufficient longitudinal length such that cutter (152) can actuate via cutter actuation assembly (150) proximally and/or distally within connector tube (182) without decoupling from connector tube (182). In the present example, connector tube (182) is configured to fluidly seal with proximal end (168) of cutter (152). By way of example only, connector tube (182) may be sized to form an interference fit with proximal end (168) of cutter (152), without preventing translation of cutter (152). In addition, or in the alternative, connector tube (182) may include one or more interior seals (not shown), such as wiper seals, dome seals, domed-wiper seals, etc. to fluidly couple connector tube (182) to proximal end (168) of cutter (152).

Seal (180) also includes an aperture (186) formed through seal (180) to fluidly couple to an outlet tube (189). In the present example, aperture (186) is parallel to and offset from connector tube (182). Aperture (186) is configured to align with a lower portion of a corresponding chamber of rotatable manifold (310), described above. Outlet tube (198) is inserted into aperture (186) at a first end and is coupled to one or more conduits (400) at a second end to fluidly couple aperture (186) to the one or more conduits (400). For instance, outlet tube (198) may be coupled to a vacuum source such that a vacuum is provided through rotatable manifold (310), cutter (152), and to lateral aperture (118). In addition, or in the alternative, outlet tube (198) may be coupled to a saline source to provide saline through cutter (152) to flush the system. Further still, outlet tube (198) may be coupled to a medicine delivery system to provide medicine out of lateral aperture (118) (e.g., anti-inflammatory medicines, pain medicines, etc.).

A central opening (187) also extends through seal (180) and is configured to permit sample holder gear (188) to extend therethrough. In some versions, central opening (187) may include seals (not shown), such as wiper seals, dome seals, domed-wiper seals, etc. to fluidly seal sample holder gear (188) and seal (180). In the present example, sample holder gear (188) is configured to engage a portion of rotatable manifold (310), such as a T-shaped axle, to rotate rotatable manifold (310) when sample holder gear (188) is rotated. As noted above, sample holder motor (280), shown in FIG. 5-6, is operable to engage and rotate rotatable manifold (310) via the meshing of sample holder cog (214) and sample holder gear (188) when probe (102) is coupled to holster (202). Still other constructions for tissue sample holder seal (180) and/or sample holder gear (188) will be apparent to one of ordinary skill in the art in view of the teachings herein.

In some versions, tissue sample holder (302) is constructed in accordance with the teachings of U.S. Non-Provisional patent application Ser. No. 13/218,656, entitled "Biopsy Device Tissue Sample Holder with Bulk Chamber and Pathology Chamber," filed Aug. 26, 2011, the disclosure of which is incorporated by reference herein. In some such versions, tissue sample holder (302) includes at least one chamber dedicated to receiving a tissue sample for testing and an additional "bulk" chamber to collect additional tissue that will not necessarily be tested. In some such versions, vacuum control module (500) may enable the operator to select between a "bulk sample" mode and an "individual sample" mode. This selection may influence which chamber of tissue sample holder (302) is aligned with lumen (136) of cutter (152) during a cutting stroke. For instance, when "bulk sample" mode is selected, motor (280) may be activated to rotate manifold (310) such that the bulk chamber is aligned with lumen (136) of cutter (152). Cutter (152) may then be actuated several times to capture several tissue samples. These samples may all be communicated to the bulk chamber. In some instances, the bulk chamber is configured such that manifold (310) may be rotated after each cutting stroke, with subsequent tissue samples still being communicated to the same bulk chamber. In addition or in the alternative, vacuum control module (500) may simply refrain from commanding motor (280) to rotate manifold (310) between cutting strokes during the "bulk sample" mode. When the operator selects "individual sample" mode, vacuum control module (500) may command motor (280) to rotate manifold (310) to align an individual tissue sample chamber with lumen (136) of cutter (152), such that the tissue sample captured in the next cutting stroke will be communicated to that individual tissue sample chamber. In some such uses of modes, an operator may first capture one tissue sample in the "individual sample" mode, then capture several (e.g., thirty) tissue samples in the "bulk sample" mode, then capture one additional tissue sample in the "individual sample" mode. Other suitable operations will be apparent to those of ordinary skill in the art in view of the teachings herein.

IV. Exemplary Blade Assembly

Figure 11:
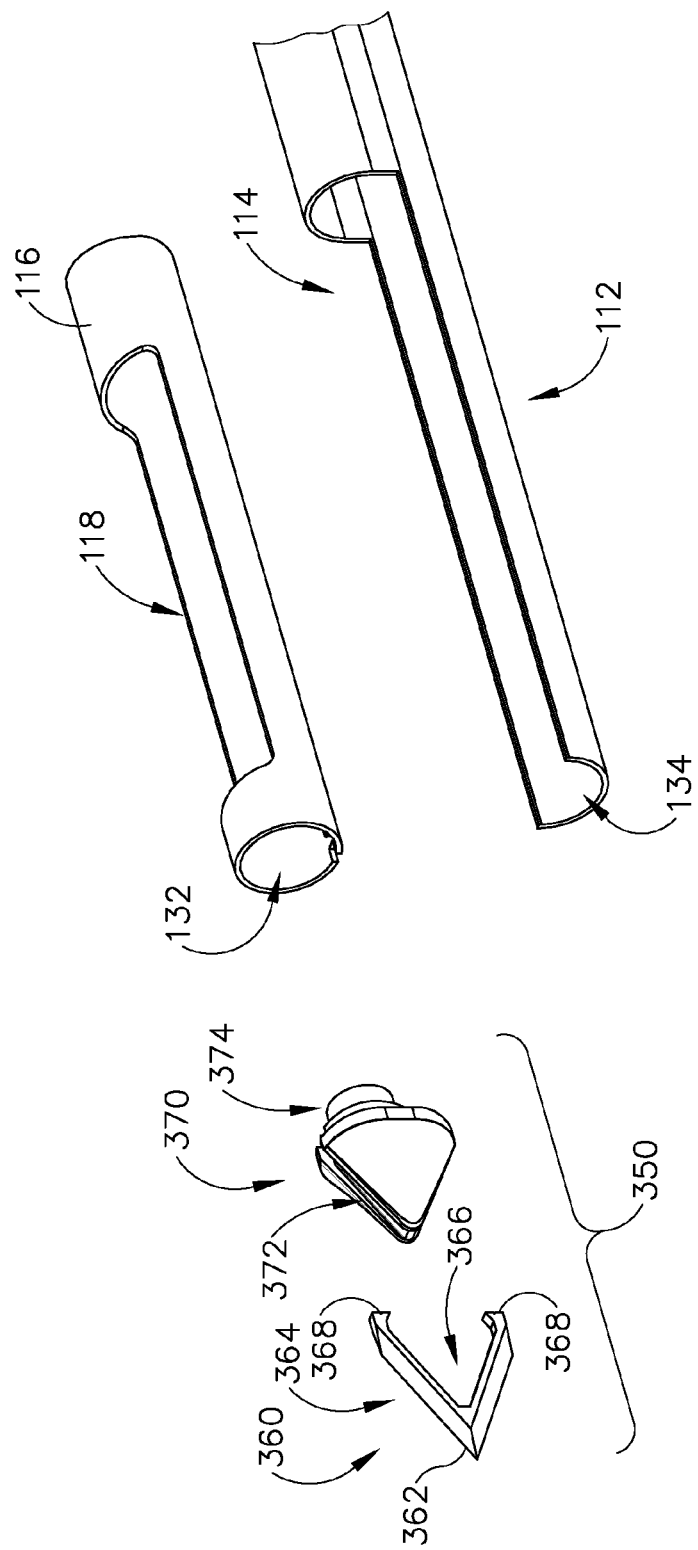
FIG. 11 depicts an enlarged perspective view of an exemplary blade assembly.
Figure 12:
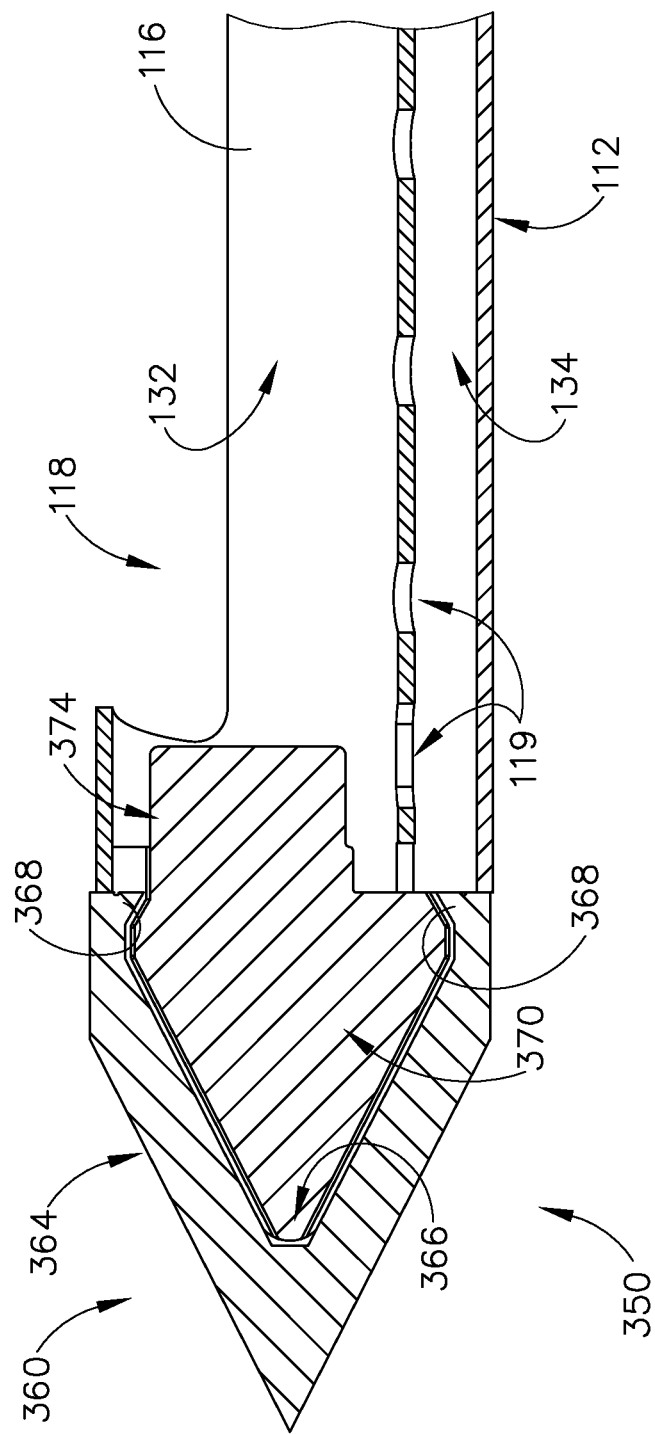
FIG. 12 depicts a side cross-sectional view of the blade assembly of FIG. 11.

Referring now to FIGS. 11-12, a blade assembly (350) is coupled to distal end (130) of needle (110). Blade assembly (350) of the present example is welded to distal end (130) of needle (110), though this is merely optional. For instance, blade assembly (350) may be mechanically or chemically coupled to distal end (130). Alternative, blade assembly (350) may simply be inserted into distal end (130) of needle (110) (e.g., by an interference fitting, etc.). Blade assembly (350) comprises a blade (360) and a nosecone (370). Blade (360) comprises a flat metallic blade having a pair of first honed surfaces (362) and second honed surfaces (364) that meet at a pair of sharp edges forming an acute angled blade tip. In the present example, blade (360) includes a pair of resilient notched ends (368) and a recess (366) formed in the proximal end of blade (360) (forming a substantially V-shaped blade). Resilient notched ends (368) are configured to snap blade (360) onto a nosecone (370), as will be described in greater detail below. Recess (366) is sized to accommodate a distal end of nosecone (370) when blade (360) is snapped onto nosecone (370). In the present example, blade (360) is a metal injection molded (MIM) component, though this is merely optional. Blade (360) may alternatively be a stamped component that is honed to provide honed surfaces (362, 364). Blade (360) may be further constructed in accordance with at least some of the teachings of U.S. Non-Provisional patent application Ser. No. 13/150,950, entitled "Needle Assembly and Blade Assembly for Biopsy Device," filed Jun. 1, 2011 and/or in any other manner as will be apparent to one of ordinary skill in the art in view of the teachings herein.

As shown in FIGS. 11-12, blade (360) is configured to snap onto nosecone (370) via resilient notched ends (368). In the present example, nosecone (370) comprises a slot (372) configured to receive blade (360) such that resilient notched end (368) can snap into a proximal recess (374) formed in nosecone (370). Nosecone (370) of the present example is also a metal injection molded (MIM) component, though this is also optional. In some versions nosecone (370) may be a plastic or ceramic component. Nosecone (370)

may be further configured in accordance with at least some of the teachings of U.S. Non-Provisional patent application Ser. No. 13/150,950, entitled "Needle Assembly and Blade Assembly for Biopsy Device," filed Jun. 1, 2011 and/or in any other manner as will be apparent to one of ordinary skill in the art in view of the teachings herein.

V. Exemplary Needle Cover

Figure 13:
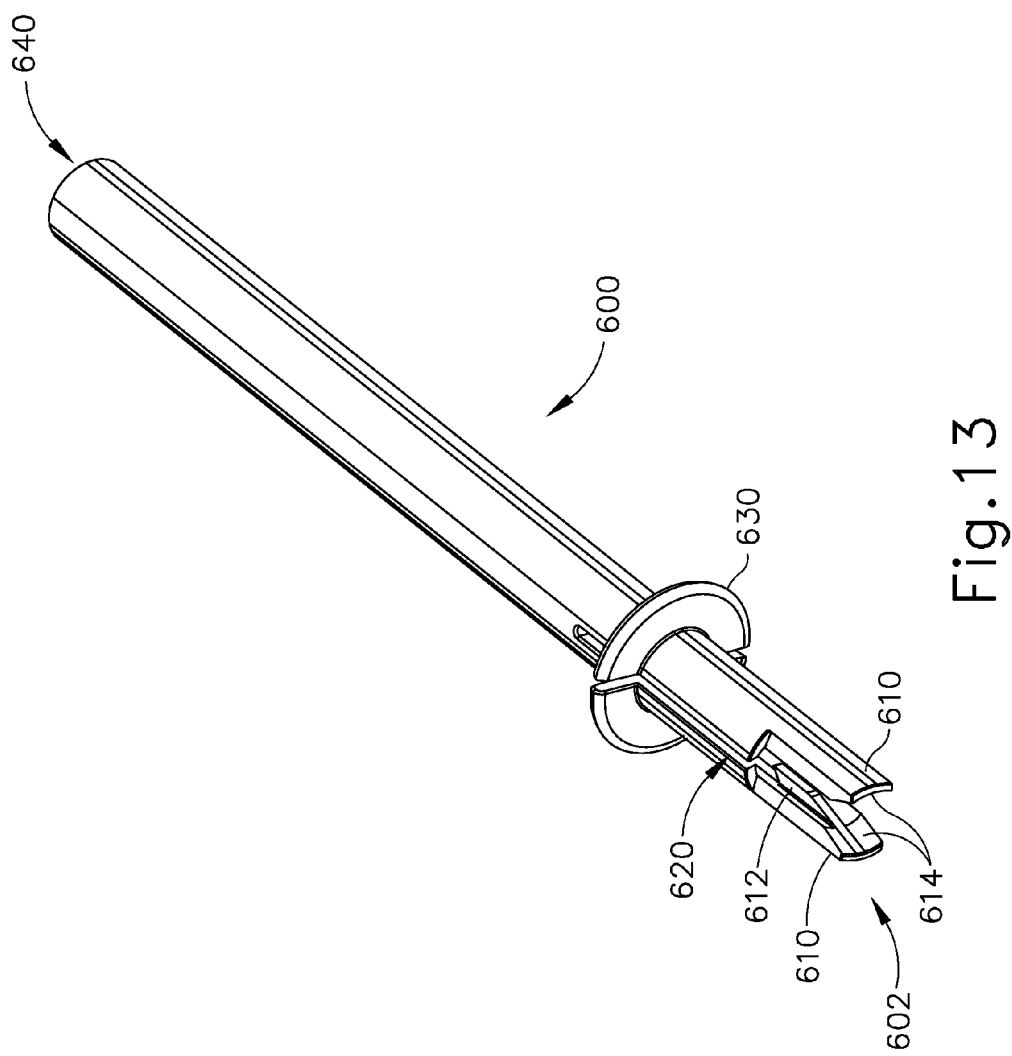
FIG. 13 depicts a perspective view of an exemplary needle tip protector.

FIG. 13 depicts an exemplary needle cover (600) configured to fit over needle (110) and blade assembly (350). In the example shown, needle cover (600) comprises a molded thermoplastic or other rigid or semi-rigid material. Needle cover (600) comprises an elongate tubular member having a closed distal end (640) and a pair of resilient tabs (610) formed at a proximal end of needle cover (600). A pair of opposing longitudinal slots (620) are formed through needle cover (600) to form resilient tabs (610). Resilient tabs (610) each comprise an inwardly extending ledge (612) and a taper (614) at the proximal end. Tapers (614) are configured to guide needle (110) and/or blade assembly (350) into needle cover (600). Ledges (612) abut needle (110) when needle cover (600) is attached to needle (110). Accordingly, ledges (612) frictionally resist needle cover (600) from detaching from needle (110). In some versions, ledges (612) may include ridging, embedded silicone nodules, rubber ratchet features, and/or other surface features to grip needle (110) when needle cover (600) is attached thereto. Resilient tabs (610) also expand outwardly when needle (110) is inserted into needle cover (600) such that an inward force is provided to assist in keeping needle cover (600) coupled to needle (110). A flange (630) is provided on the exterior of needle cover (600) for a user to grasp when removing or attaching needle cover (600) to needle (110) and/or blade assembly (350). Of course still further configurations for needle cover (600) will be apparent to one of ordinary skill in the art in view of the teachings herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Embodiments of the devices disclosed herein can be reconditioned for reuse after at least one use. Reconditioning may include any combination of the steps of disassembly of the device, followed by cleaning or replacement of particular pieces, and subsequent reassembly. In particular, embodiments of the devices disclosed herein may be disassembled, and any number of the particular pieces or parts of the devices may be selectively replaced or removed in any combination. Upon cleaning and/or replacement of particular parts, embodiments of the devices may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A biopsy device, comprising:
   (a) a probe portion, wherein the probe portion comprises:
      (i) a probe body,
      (ii) a needle extending distally from the probe body, wherein the needle defines a longitudinal axis,
      (iii) a cutter movable relative to the needle to sever tissue, and
      (iv) a tissue sample holder; and
   (b) a holster portion, wherein the holster portion comprises:
      (i) a holster body, wherein the holster body includes a probe coupling feature and a probe securing feature, wherein the probe coupling feature comprises a recess having a lateral portion and a longitudinal portion, wherein the probe securing feature defines a side loading opening between the probe securing feature and an upwardly facing surface of the holster body, wherein the side loading opening is configured to receive the probe body along a lateral path relative to the longitudinal axis of the needle to laterally align the probe portion relative to the holster portion, and
      (ii) a cutter drive feature operable to drive the cutter.

2. The biopsy device of claim 1, wherein the probe portion further includes a first cutter drive gear, wherein the cutter drive feature of the holster portion further includes a second cutter drive gear, wherein the first and second cutter drive gears are configured to mesh upon receipt of at least a portion of the probe body in the probe securing feature.

3. The biopsy device of claim 2, wherein the first cutter drive gear is configured to slide laterally within the lateral portion of the probe coupling feature during coupling of the probe body with the holster body.

4. The biopsy device of claim 2, wherein the first cutter drive gear is configured to slide longitudinally within the longitudinal portion of the probe coupling feature during coupling of the probe body with the holster body.

5. The biopsy device of claim 1, wherein the holster body comprises at least one protrusion configured to engage the probe body to thereby maintain a distance between a gear of the probe portion and a gear of the holster portion.

6. The biopsy device of claim 1, wherein the holster body further comprises a channel, wherein the probe body further comprises a latch, wherein the latch is configured to slide distally within the channel during coupling of the probe body with the holster body.

7. The biopsy device of claim 1, wherein the holster body includes a proximal portion and a distal portion, wherein the probe securing feature is located at the distal portion of the holster body.

8. The biopsy device of claim 1, wherein the holster portion further comprises at least one button operable to activate the cutter drive feature.

9. The biopsy device of claim 8, wherein the at least one button is located on the probe securing feature.

10. The biopsy device of claim 1, wherein the probe securing feature is configured to enable the probe body to slide longitudinally relative to the holster body for receipt of at least a portion of the probe body in the probe securing feature.

11. The biopsy device of claim 1, further comprising a latch, wherein the latch is configured to secure a longitudinal position of the probe body relative to the holster body upon receipt of at least a portion of the probe body in the probe securing feature.

12. The biopsy device of claim 11, wherein the probe securing feature is configured to prevent distal and lateral movement of the probe body relative to the holster portion upon receipt of the at least a portion of the probe body in the probe securing feature, wherein the latch is configured to prevent proximal movement of the probe body relative to the holster portion upon receipt of the at least a portion of the probe body in the probe securing feature.

13. The biopsy device of claim 1, wherein the cutter drive feature of the holster portion includes a motor housed within the holster body.

14. The biopsy device of claim 1, wherein the tissue sample holder comprises a plurality of chambers operable to receive a plurality of tissue samples, wherein the tissue sample holder comprises a rotatable feature operable to selectively index the chambers for serial receipt of tissue samples.

15. The biopsy device of claim 14, wherein the rotatable feature comprises a manifold.

16. The biopsy device of claim 14, wherein the tissue sample holder comprises a removable tray associated with the chambers, wherein the removable tray is operable to hold tissue samples received in the chambers, wherein the removable tray is removable from the tissue sample holder.

17. The biopsy device of claim 14, wherein the holster portion further comprises a tissue sample holder drive feature operable to rotate the rotatable feature of the tissue sample holder.

18. A biopsy device, comprising:
(a) a probe portion, wherein the probe portion comprises:
(i) a probe body comprising a first cutter drive gear rotatable about a first axis, wherein the probe body further comprises a proximal portion and a distal portion,
(ii) a needle extending distally from the probe body, wherein the needle defines a longitudinal axis,
(iii) a cutter movable relative to the needle to sever tissue, and
(iv) a tissue sample holder; and
(b) a holster portion removably coupled with the probe portion, wherein the holster portion comprises:
(i) a holster body,
(ii) a second cutter drive gear configured to mesh with the first cutter drive gear, wherein the second cutter drive gear is rotatable about a second axis,
(iii) a probe coupling feature comprising a recess, wherein the recess is configured to receive the first cutter drive gear of the probe body such that the first cutter drive gear is configured to translate within the recess until the first cutter drive gear is aligned with the second cutter drive gear, and
(iv) a probe securing feature, wherein the probe securing feature defines a lateral opening between the probe securing feature and the holster body, wherein the lateral opening is configured to receive the distal portion of the probe body along a path that is transverse to the longitudinal axis of the needle, wherein the probe securing feature comprises locating features that are configured to locate the probe portion relative to the holster portion when the proximal portion of the probe body is received within the lateral opening.

19. The biopsy device of claim 18, wherein the holster portion further comprises at least one setoff feature operable to engage the probe body to maintain distance between the first axis and the second axis.

20. A biopsy device, comprising:
(a) a probe portion, wherein the probe portion comprises:
(i) a probe body,
(ii) a latch extending downwardly from the probe body,
(iii) a needle extending distally from the probe body, wherein the needle defines a longitudinal axis,
(iv) a cutter movable relative to the needle to sever tissue, and
(v) a tissue sample holder; and
(b) a holster portion removably coupled with the probe portion, wherein the holster portion comprises:
(i) a holster body,
(ii) a channel, wherein the latch of the probe body is configured to translate within the channel of the holster portion during coupling of the probe portion with the holster portion, and
(iii) a probe coupling feature, wherein the probe coupling feature is configured to receive the latch of the probe portion to secure a longitudinal position of the probe portion relative to the holster portion, and
(iv) a probe securing feature positioned distally of the probe coupling feature, wherein the probe securing feature defines an opening between the probe securing feature and the holster body, wherein the opening is configured to laterally receive at least a portion of the probe body to secure a lateral position of the probe portion relative to the holster portion, wherein the lateral position of the probe portion is oriented in a direction orthogonal to the longitudinal axis of the needle.

* * * * *